(12) United States Patent
Grumolato

(10) Patent No.: US 11,371,040 B2
(45) Date of Patent: Jun. 28, 2022

(54) ENDONUCLEASE-BARCODING

(71) Applicants: Institut National de la Sante et de la Recherche Medicale (INSERM), Paris (FR); Universite de Rouen Normandie, Mont-Saint-Aignan (FR)

(72) Inventor: Luca Grumolato, Mont-Saint-Aignan (FR)

(73) Assignees: INSTITUT NATIONAL DE LA SANTE ET DE LA RECHERCHE MEDICAL (INSERM), Paris (FR); UNIVERSITE DE ROUEN NORMANDIE, Mont-Saint-Aignan (FR)

( * ) Notice: Subject to any disclaimer, the term of this patent is extended or adjusted under 35 U.S.C. 154(b) by 128 days.

(21) Appl. No.: 15/769,585

(22) PCT Filed: Oct. 21, 2016

(86) PCT No.: PCT/EP2016/075370
§ 371 (c)(1),
(2) Date: Apr. 19, 2018

(87) PCT Pub. No.: WO2017/068120
PCT Pub. Date: Apr. 27, 2017

(65) Prior Publication Data
US 2018/0312831 A1    Nov. 1, 2018

(30) Foreign Application Priority Data
Oct. 22, 2015 (EP) .................................. 15306698

(51) Int. Cl.
C12N 15/10   (2006.01)
C12Q 1/6816  (2018.01)

(52) U.S. Cl.
CPC ....... *C12N 15/1065* (2013.01); *C12Q 1/6816* (2013.01)

(58) Field of Classification Search
None
See application file for complete search history.

(56) References Cited

U.S. PATENT DOCUMENTS 8,697,359 B1 * 4/2014 Zhang ...................... C12N 9/96
                                                          435/6.1
2014/0068797 A1   3/2014 Doudna et al.

FOREIGN PATENT DOCUMENTS

WO   2015/065964 A1   5/2015
WO   2015123339 A1    8/2015
WO   2015/138855 A1   9/2015

OTHER PUBLICATIONS

Kim et al., Highly efficient RNA-guided genome editing in human cells via delivery of purified Cas9 ribonucleoproteins, Genome Research, vol. 24, pp. 1012-1019 (Year: 2014).*
Blundell et al., Beyond genome sequencing: Lineage tracking with barcodes to study the dynamics of evolution, infection, and cancer, Genomics, 2014, pp. 417-430 (Year: 2014).*
Irion et al. "Precise and efficient genome editing in zebrafish using the CRISPR/Cas9 system" 141 Development 4827-4830 (Year: 2014).*
Barrangou et al.; "CRISPR-Cas Systems: Prokaryotes Upgrade to Adaptive Immunity"; Molecular Cell 54, Apr. 24, 2014, pp. 234-244.
Doudna et al.; "The new frontier of genome engineering with CRISPR-Cas9"; Science, vol. 346, issue 6213, Nov. 28, 2014, entire article.
Grumolato et al.; "beta-Catenin-Independent Activation of TCF1/LEF1 in Human Hematopoietic Tumor Cells through Interaction with ATF2 Transcription Factors"; PLOS Genetics, vol. 1, issue 8, Aug. 2013, pp. 1-13.
Hsu et al.; "Development and Applications of CRISPR-Cas9 for Genome Engineering"; Cell 157, Jun. 5, 2014, pp. 1262-1278.
Lin et al.; "CRISPR/Cas9 systems have off-target activity with insertions or deletions between target DNA and guide RNA sequences"; Nucleic Acids Research, vol. 42, No. 11, 2014, pp. 7473-7485.
Matsuda et al.; "Controlled expression of transgenes introduced by in vivo electroporation"; PNAS, vol. 104, No. 3, Jan. 16, 2007, pp. 1027-1032.
Pfaffl et al.; "A new mathematical model for relative quantification in real-time RT-PCR"; Nucleic Acids Research, vol. 29, No. 9, 2001.
Ran et al.; "Genome engineering using the CRISPR-Cas9 system"; Nature Protocol, Nov. 2013, vol. 8, No. 11, pp. 2281-2308.
Wang et al.; "Unbiased detection of off-target cleavage by CRISPR-Cas9 and TALENs using integrase-defective lentiviral vectors"; Nature Biotechnology, vol. 33, Jan. 19, 2015, pp. 175-178.
Bell et al.; "A high-throughput screening strategy for detecting CRISPR-Cas9 induced mutations using next-generation sequencing"; BMC Genomics, vol. 15, No. 1, Nov. 20, 2014, p. 1002, the whole article.
Maggio et al.; "Genome editing at the crossroads of delivery, specificity, and fidelity"; Trends in Biotechnology, vol. 33, No. 5, May 1, 2015, pp. 280-291.
Fu et al., "Improving CRISPR-Cas nuclease specificity using truncated guide RNAs", Nature Biotechnology, Jan. 26, 2014.
Shah et al., "The clonal and mutational evolution spectrum of primary triple-negative breast cancers", Nature, vol. 486, Jun. 21, 2012, p. 395-399.

* cited by examiner

Primary Examiner — Nancy J Leith
(74) Attorney, Agent, or Firm — WCF IP

(57) ABSTRACT

Provided herein are methods and kits for labeling endonuclease-treated cells. The methods comprise: contacting the cells to be labelled with at least one endonuclease suitable for targeting a genomic region of interest, and first and second nucleic acids suitable for introducing one or more silent (or optionally non-silent) mutation(s) in the genomic region by homology-directed repair (HDR). The mutation(s) introduced by the first nucleic acid differ from the mutation(s) introduced by the second nucleic acid.

7 Claims, 11 Drawing Sheets
Specification includes a Sequence Listing.

SEQUENCE LISTING

<160> NUMBER OF SEQ ID NOS: 72

<210> SEQ ID NO 1
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 1
agggctatct ggaagatcac        20

<210> SEQ ID NO 2
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 2
ccatgcagtg gaatggtaag        20

<210> SEQ ID NO 3
<211> LENGTH: 20

```
<212> TYPE: DNA
<213> ORGANISM: Artificial Sequence
<220> FEATURE:
<223> OTHER INFORMATION: Synthetic sgRNA

<400> SEQUENCE: 3
gggcagctac ggtttccgtc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 4
cagaatgcaa gaagcccaga                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 5
tgcagcgaac aatgttctgg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 6
agaacattgt tcgctgcatt                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 7
ctgcgtgatg agctgcacgg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 8
gagctgcgtg atgagctgca                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 9
```
gaatataaac ttgtggtagt				20

<210> SEQ ID NO 10
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 10
cttgtggtag ttggagctgg				20

<210> SEQ ID NO 11
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 11
gacctgaaca gcaagtttgt				20

<210> SEQ ID NO 12
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 12
ggccttgctg aaacttcctt				20

<210> SEQ ID NO 13
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 13
gtcccctcca ccccacagtg				20

<210> SEQ ID NO 14
<211> LENGTH: 20
<212> TYPE: DNA
<213> ORGANISM: Artificial Sequence
<220> FEATURE:
<223> OTHER INFORMATION: Synthetic sgRNA

<400> SEQUENCE: 14
gtcaccaatc ctgtccctag				20

<210> SEQ ID NO 15
<211> LENGTH: 162
<212> TYPE: DNA
<213> ORGANISM: Artificial Sequence
<220> FEATURE:
<223> OTHER INFORMATION: Synthetic ssDNA

<400> SEQUENCE: 15
cacttgatag ttttgagagt cgttcgattg ccagctccgt tcagagtgaa ccatgcagtg		60 gaatggtaag tgcgatcatt agtccgagcg accttccaga tagccctgga caaaccatgc		120 caccaagcag aagtaaaaca cctccaccac ctcctcaaac ag		162

<210> SEQ ID NO 16
<211> LENGTH: 161
<212> TYPE: DNA
<213> ORGANISM: Artificial Sequence
<220> FEATURE:
<223> OTHER INFORMATION: Synthetic ssDNA

<400> SEQUENCE: 16

```
cacttgatag ttttgagagt cgttcgattg ccagctccgt tcagagtgaa ccatgcagtg      60
gaatggtaag ttgactcgag aattcagtga tcttccagat agccctggac aaaccatgcc     120
accaagcaga agtaaaacac ctccaccacc tcctcaaaca g                         161
```

<210> SEQ ID NO 17
<211> LENGTH: 186
<212> TYPE: DNA
<213> ORGANISM: Artificial Sequence
<220> FEATURE:
<223> OTHER INFORMATION: Synthetic ssDNA

<400> SEQUENCE: 17

```
ctcctacacc ggcggcccct gcaccagccc cctcctggcc cctgtcatct tctgtccctt      60
cccagaaaac ctaccagggc agctatggct ttcgcctcgg attcttgcat tctgggacag     120
ccaagtctgt gacttgcacg gtcagttgcc ctgaggggct ggcttccatg agacttcaat     180
gcctgg                                                                186
```

<210> SEQ ID NO 18
<211> LENGTH: 185
<212> TYPE: DNA
<213> ORGANISM: Artificial Sequence
<220> FEATURE:
<223> OTHER INFORMATION: Synthetic ssDNA

<400> SEQUENCE: 18

```
ctcctacacc ggcggcccct gcaccagccc cctcctggcc cctgtcatct tctgtccctt      60
cccagaaaac ctaccagggc agctacggtt gagaattctc ttcttgcatt ctgggacagc     120
caagtctgtg acttgcacgg tcagttgccc tgaggggctg gcttccatga gacttcaatg     180
cctgg                                                                 185
```

<210> SEQ ID NO 19
<211> LENGTH: 173
<212> TYPE: DNA
<213> ORGANISM: Artificial Sequence
<220> FEATURE:
<223> OTHER INFORMATION: Synthetic ssDNA

<400> SEQUENCE: 19

```
gtaactttgt atcctgttcc tcccagttta agatttgccc agactcagct cagttaattt      60
tggttacatc cctctctgct ctgcagcaag tttaatcatc aaaacatagt tcgctgcatt     120
ggagtgagcc tgcaatccct gccccggttc atcctgctgg agctcatggc ggg            173
```

<210> SEQ ID NO 20
<211> LENGTH: 173
<212> TYPE: DNA
<213> ORGANISM: Artificial Sequence
<220> FEATURE:
<223> OTHER INFORMATION: Synthetic ssDNA

<400> SEQUENCE: 20

```
gtaactttgt atcctgttcc tcccagttta agatttgccc agactcagct cagttaattt      60
```
tggttacatc cctctctgct ctgcagcaaa ttaaatcatc agaatatcgt ccgctgcatt    120
ggagtgagcc tgcaatccct gccccggttc atcctgctgg agctcatggc ggg    173

<210> SEQ ID NO 21
<211> LENGTH: 174
<212> TYPE: DNA
<213> ORGANISM: Artificial Sequence
<220> FEATURE:
<223> OTHER INFORMATION: Synthetic ssDNA

<400> SEQUENCE: 21
gtaactttgt atcctgttcc tcccagttta agatttgccc agactcagct cagttaattt    60
tggttacatc cctctctgct ctgcagcaaa tagtgaatta tcgaacattg ttcgctgcat    120
tgaggtgagc ctgcaatccc tgccccggtt catcctgctg gagctcatgg cggg    174

<210> SEQ ID NO 22
<211> LENGTH: 173
<212> TYPE: DNA
<213> ORGANISM: Artificial Sequence
<220> FEATURE:
<223> OTHER INFORMATION: Synthetic ssDNA

<400> SEQUENCE: 22
gtaactttgt atcctgttcc tcccagttta agatttgccc agactcagct cagttaattt    60
tggttacatc cctctctgct ctgcagcaag ttaaatcatc aaaacatagt tcgctgcatt    120
ggagtgagcc tgcaatccct gccccggttc atcctgctgg agctcatggc ggg    173

<210> SEQ ID NO 23
<211> LENGTH: 173
<212> TYPE: DNA
<213> ORGANISM: Artificial Sequence
<220> FEATURE:
<223> OTHER INFORMATION: Snythetic ssDNA

<400> SEQUENCE: 23
gtaactttgt atcctgttcc tcccagttta agatttgccc agactcagct cagttaattt    60
tggttacatc cctctctgct ctgcagcaaa tttaatcatc agaatatcgt ccgttgcatt    120
ggagtgagcc tgcaatccct gccccggttc atcctgctgg agctcatggc ggg    173

<210> SEQ ID NO 24
<211> LENGTH: 188
<212> TYPE: DNA
<213> ORGANISM: Artificial Sequence
<220> FEATURE:
<223> OTHER INFORMATION: Synthetic ssDNA

<400> SEQUENCE: 24
ctccctccct ccaggaagcc tacgtgatgg ccagcgtgga caacccccac gtgtgccgcc    60
tgctgggcat ctgcctcacc tctacagtcc aactgattac ccagctcatg cccttcggct    120
gcctcctgga ctatgtccgg gaacacaaag acaatattgg ctcccagtac ctgctcaact    180
ggtgtgtg    188

<210> SEQ ID NO 25
<211> LENGTH: 188
<212> TYPE: DNA
<213> ORGANISM: Artificial Sequence
<220> FEATURE:
<223> OTHER INFORMATION: Snythetic ssDNA

<400> SEQUENCE: 25
ctccctccct ccaggaagcc tacgtgatgg ccagcgtgga caaccccac gtgtgccgcc    60 tgctgggcat ctgcctcacc tctactgtac agcttataat gcaactgatg cccttcggct   120
gcctcctgga ctatgtccgg gaacacaaag acaatattgg ctcccagtac ctgctcaact   180
ggtgtgtg                                                            188

<210> SEQ ID NO 26
<211> LENGTH: 184
<212> TYPE: DNA
<213> ORGANISM: Artificial Sequence
<220> FEATURE:
<223> OTHER INFORMATION: Synthetic ssDNA

<400> SEQUENCE: 26
taaccttatg tgtgacatgt tctaatatag tcacattttc attattttta ttataaggcc    60
tgctgaaaat gactgaatat aagttggtag tggttggcgc aggaggcgta ggcaagagtg   120
ccttgacgat acagctaatt cagaatcatt ttgtggacga atatgatcca acaatagagg   180
taaa                                                                184

<210> SEQ ID NO 27
<211> LENGTH: 184
<212> TYPE: DNA
<213> ORGANISM: Artificial Sequence
<220> FEATURE:
<223> OTHER INFORMATION: Synthetic ssDNA

<400> SEQUENCE: 27
taaccttatg tgtgacatgt tctaatatag tcacattttc attattttta ttataaggcc    60
tgctgaaaat gactgaatat aagttagttg tcgttggtgc cgacggcgta ggcaagagtg   120
ccttgacgat acagctaatt cagaatcatt ttgtggacga atatgatcca acaatagagg   180
taaa                                                                184

<210> SEQ ID NO 28
<211> LENGTH: 180
<212> TYPE: DNA
<213> ORGANISM: Artificial Sequence
<220> FEATURE:
<223> OTHER INFORMATION: Synthetic ssDNA

<400> SEQUENCE: 28
agtgaacaca gttgtgttgt tcaatttta aggtattttt agatgataaa tattgatgta    60
agtggagaca gttgacctga acagcaagtt cttaggctcc atggcaccca gggtgcttcc   120
acccaacctt ccctccctcc ctcgttcacg tggggttata cttgcaacac agtctgctgg   180

<210> SEQ ID NO 29
<211> LENGTH: 194
<212> TYPE: DNA
<213> ORGANISM: Artificial Sequence
<220> FEATURE:
<223> OTHER INFORMATION: Synthetic ssDNA, n = A, C, G or T
<220> FEATURE:
<221> NAME/KEY: misc_feature
<222> LOCATION: (91)..(95)
<223> OTHER INFORMATION: n is a, c, g, or t
<220> FEATURE:
<221> NAME/KEY: misc_feature
<222> LOCATION: (98)..(101)
<223> OTHER INFORMATION: n is a, c, g, or t

<400> SEQUENCE: 29

```
gtgtccccga gctgggacca ccttatattc ccagggccgg ttaatgtggc tctggttctg    60
ggtactttta tctgtcccct ccaccccaca nnnnnatnnn ngtcgacagg attggtgaca   120
gaaaagcccc atccttaggc ctcctccttc ctagtctcct gatattgggt ctaaccccca   180
cctcctgtta ggca                                                    194
```

```
<210> SEQ ID NO 30
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 30
gctgaagatc ctgtgagcga                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 31
ttgtgcctgg ctgattctga                                               20

<210> SEQ ID NO 32
<211> LENGTH: 22
<212> TYPE: DNA
<213> ORGANISM: Artificial Sequence
<220> FEATURE:
<223> OTHER INFORMATION: Synthetic ssDNA

<400> SEQUENCE: 32
agaccccact catgtttagc ag                                            22

<210> SEQ ID NO 33
<211> LENGTH: 21
<212> TYPE: DNA
<213> ORGANISM: Artificial Sequence
<220> FEATURE:
<223> OTHER INFORMATION: Synthetic ssDNA

<400> SEQUENCE: 33
ggtcgctcgg actaatgatc g                                             21

<210> SEQ ID NO 34
<211> LENGTH: 25
<212> TYPE: DNA
<213> ORGANISM: Artificial Sequence
<220> FEATURE:
<223> OTHER INFORMATION: Synthetic ssDNA

<400> SEQUENCE: 34
ggaagatcac tgaattctcg agtca                                         25

<210> SEQ ID NO 35
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 35
gacccagggt tggaagtgtc                                               20
```

<210> SEQ ID NO 36
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 36
ctaggatctg actgcggctc                                           20

<210> SEQ ID NO 37
<211> LENGTH: 21
<212> TYPE: DNA
<213> ORGANISM: Artificial Sequence
<220> FEATURE:
<223> OTHER INFORMATION: Synthetic ssDNA

<400> SEQUENCE: 37
caggtccaga tgaagctccc a                                         21

<210> SEQ ID NO 38
<211> LENGTH: 19
<212> TYPE: DNA
<213> ORGANISM: Artificial Sequence
<220> FEATURE:
<223> OTHER INFORMATION: Synthetic ssDNA

<400> SEQUENCE: 38
gaatccgagg cgaaagcca                                            19

<210> SEQ ID NO 39
<211> LENGTH: 26
<212> TYPE: DNA
<213> ORGANISM: Artificial Sequence
<220> FEATURE:
<223> OTHER INFORMATION: Synthetic ssDNA

<400> SEQUENCE: 39
tcccagaatg caagaagaga attctc                                    26

<210> SEQ ID NO 40
<211> LENGTH: 23
<212> TYPE: DNA
<213> ORGANISM: Artificial Sequence
<220> FEATURE:
<223> OTHER INFORMATION: Synthetic ssDNA

<400> SEQUENCE: 40
gcccatgttt acagaatgcc ttt                                       23

<210> SEQ ID NO 41
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 41
ccccaatgca gcgaacaatg                                           20

<210> SEQ ID NO 42
<211> LENGTH: 28
<212> TYPE: DNA
<213> ORGANISM: Artificial Sequence
<220> FEATURE:

<223> OTHER INFORMATION: Synthetic ssDNA

<400> SEQUENCE: 42
gcagcgaact atgttttgat gattaaac                                28

<210> SEQ ID NO 43
<211> LENGTH: 23
<212> TYPE: DNA
<213> ORGANISM: Artificial Sequence
<220> FEATURE:
<223> OTHER INFORMATION: Synthetic ssDNA

<400> SEQUENCE: 43
caatgcaacg gacgatattc tga                                     23

<210> SEQ ID NO 44
<211> LENGTH: 26
<212> TYPE: DNA
<213> ORGANISM: Artificial Sequence
<220> FEATURE:
<223> OTHER INFORMATION: Synthetic ssDNA

<400> SEQUENCE: 44
cagcgaacaa tgttcgataa ttcact                                  26

<210> SEQ ID NO 45
<211> LENGTH: 28
<212> TYPE: DNA
<213> ORGANISM: Artificial Sequence
<220> FEATURE:
<223> OTHER INFORMATION: Synthetic ssDNA

<400> SEQUENCE: 45
gcagcgaact atgttttgat gatttaac                                28

<210> SEQ ID NO 46
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 46
tgcttccccc attcaggact                                         20

<210> SEQ ID NO 47
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 47
ctccttgcac ctcctcactg                                         20

<210> SEQ ID NO 48
<211> LENGTH: 22
<212> TYPE: DNA
<213> ORGANISM: Artificial Sequence
<220> FEATURE:
<223> OTHER INFORMATION: Synthetic ssDNA

<400> SEQUENCE: 48
ccttccctga ttacctttgc ga                                      22

```
<210> SEQ ID NO 49
<211> LENGTH: 25
<212> TYPE: DNA
<213> ORGANISM: Artificial Sequence
<220> FEATURE:
<223> OTHER INFORMATION: Synthetic ssDNA

<400> SEQUENCE: 49
cacctctaca gtccaactga ttacc                                              25

<210> SEQ ID NO 50
<211> LENGTH: 28
<212> TYPE: DNA
<213> ORGANISM: Artificial Sequence
<220> FEATURE:
<223> OTHER INFORMATION: Synthetic ssDNA

<400> SEQUENCE: 50
ctctactgta cagcttataa tgcaactg                                           28

<210> SEQ ID NO 51
<211> LENGTH: 22
<212> TYPE: DNA
<213> ORGANISM: Artificial Sequence
<220> FEATURE:
<223> OTHER INFORMATION: Synthetic ssDNA

<400> SEQUENCE: 51
atcctttgag agcctttagc cg                                                 22

<210> SEQ ID NO 52
<211> LENGTH: 21
<212> TYPE: DNA
<213> ORGANISM: Artificial Sequence
<220> FEATURE:
<223> OTHER INFORMATION: Synthetic ssDNA

<400> SEQUENCE: 52
ccagttgact gcagacgtgt a                                                  21

<210> SEQ ID NO 53
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 53
ctgcgccaac cactaccaac                                                    20

<210> SEQ ID NO 54
<211> LENGTH: 19
<212> TYPE: DNA
<213> ORGANISM: Artificial Sequence
<220> FEATURE:
<223> OTHER INFORMATION: Synthetic ssDNA

<400> SEQUENCE: 54
gtcggcacca acgacaact                                                     19

<210> SEQ ID NO 55
<211> LENGTH: 29
<212> TYPE: DNA
<213> ORGANISM: Artificial Sequence
<220> FEATURE:
<223> OTHER INFORMATION: Synthetic ssDNA
```

<400> SEQUENCE: 55
tattaaaagg tactggtgga gtatttgat                                29

<210> SEQ ID NO 56
<211> LENGTH: 24
<212> TYPE: DNA
<213> ORGANISM: Artificial Sequence
<220> FEATURE:
<223> OTHER INFORMATION: Synthetic ssDNA

<400> SEQUENCE: 56
ctcgtggtaa catcagaaca gaga                                     24

<210> SEQ ID NO 57
<211> LENGTH: 22
<212> TYPE: DNA
<213> ORGANISM: Artificial Sequence
<220> FEATURE:
<223> OTHER INFORMATION: Synthetic ssDNA

<400> SEQUENCE: 57
tgccatggag cctaagaact tg                                       22

<210> SEQ ID NO 58
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 58
agctgaagat cctgtgagcg                                          20

<210> SEQ ID NO 59
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 59
aatggctcat cgaggctcag                                          20

<210> SEQ ID NO 60
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 60
catcttccag gggtccgaga                                          20

<210> SEQ ID NO 61
<211> LENGTH: 20
<212> TYPE: DNA
<213> ORGANISM: Artificial Sequence
<220> FEATURE:
<223> OTHER INFORMATION: Synthetic ssDNA

<400> SEQUENCE: 61
tcagtgaaac gcaccagacg                                          20

<210> SEQ ID NO 62
<211> LENGTH: 19

```
<212> TYPE: DNA
<213> ORGANISM: Artificial Sequence
<220> FEATURE:
<223> OTHER INFORMATION: Synthetic ssDNA

<400> SEQUENCE: 62
gattgccagc tccgttcag                                                    19

<210> SEQ ID NO 63
<211> LENGTH: 22
<212> TYPE: DNA
<213> ORGANISM: Artificial Sequence
<220> FEATURE:
<223> OTHER INFORMATION: Synthetic ssDNA

<400> SEQUENCE: 63
atttactgca gcttgcttag gt                                                22

<210> SEQ ID NO 64
<211> LENGTH: 19
<212> TYPE: DNA
<213> ORGANISM: Artificial Sequence
<220> FEATURE:
<223> OTHER INFORMATION: Synthetic ssDNA

<400> SEQUENCE: 64
tgctcagaca cccaaaagt                                                    19

<210> SEQ ID NO 65
<211> LENGTH: 21
<212> TYPE: DNA
<213> ORGANISM: Artificial Sequence
<220> FEATURE:
<223> OTHER INFORMATION: Synthetic ssDNA

<400> SEQUENCE: 65
gttttacttc tgcttggtgg c                                                 21

<210> SEQ ID NO 66
<211> LENGTH: 80
<212> TYPE: DNA
<213> ORGANISM: Artificial Sequence
<220> FEATURE:
<223> OTHER INFORMATION: Synthetic ssDNA

<400> SEQUENCE: 66
aatgatacgg cgaccaccga gatctacact ctttccctac acgacgctct tccgatctgt       60
taatgtggct ctggttctgg                                                   80

<210> SEQ ID NO 67
<211> LENGTH: 86
<212> TYPE: DNA
<213> ORGANISM: Artificial Sequence
<220> FEATURE:
<223> OTHER INFORMATION: Synthetic ssDNA

<400> SEQUENCE: 67
caagcagaag acggcatacg agatcgtgat gtgactggag ttcagacgtg tgctcttccg       60
atctggtggg ggttagaccc aatatc                                            86

<210> SEQ ID NO 68
<211> LENGTH: 19
<212> TYPE: DNA
<213> ORGANISM: Artificial Sequence
<220> FEATURE:
```

```
<223> OTHER INFORMATION: Synthetic ssDNA

<400> SEQUENCE: 68
tccctccagg aagcctacg                                              19

<210> SEQ ID NO 69
<211> LENGTH: 22
<212> TYPE: DNA
<213> ORGANISM: Artificial Sequence
<220> FEATURE:
<223> OTHER INFORMATION: Synthetic ssDNA

<400> SEQUENCE: 69
ccttccctga ttacctttgc ga                                          22

<210> SEQ ID NO 70
<211> LENGTH: 25
<212> TYPE: DNA
<213> ORGANISM: Artificial Sequence
<220> FEATURE:
<223> OTHER INFORMATION: Synthetic ssDNA

<400> SEQUENCE: 70
ccaactgatt acccagctca tgccc                                       25

<210> SEQ ID NO 71
<211> LENGTH: 27
<212> TYPE: DNA
<213> ORGANISM: Artificial Sequence
<220> FEATURE:
<223> OTHER INFORMATION: Synthetic ssDNA

<400> SEQUENCE: 71
gcttataatg caactgatgc ccttcgg                                     27

<210> SEQ ID NO 72
<211> LENGTH: 24
<212> TYPE: DNA
<213> ORGANISM: Artificial Sequence
<220> FEATURE:
<223> OTHER INFORMATION: Synthetic ssDNA

<400> SEQUENCE: 72
tccaccgtgc agctcatcac gcag                                        24
```

ENDONUCLEASE-BARCODING

SEQUENCE LISTING

This application includes as the Sequence Listing the complete contents of the accompanying text file "SequenceListing_ST25.txt", created Apr. 17, 2018, containing 17050 bytes, hereby incorporated by reference.

FIELD OF THE INVENTION

The invention relates to methods, compositions and kits for labelling and detecting endonuclease-treated cells, and most preferably eukaryotic cells.

BACKGROUND OF THE INVENTION

In the last few years, staggering advances in sequencing technologies have provided an unprecedentedly detailed overview of the multiple genetic aberrations in cancer. By considerably expanding the list of new potential oncogenes and tumor suppressor genes, these new data strongly emphasize the need of fast and reliable strategies to characterize the normal and pathological function of these genes and assess their role, in particular as driving factors during oncogenesis.

As an alternative to more conventional approaches, such as cDNA overexpression or downregulation by RNA interference, the new technologies for DNA editing provide the means to recreate the actual mutations observed in cancer through direct manipulation of the genome.

Indeed, natural and engineered nuclease enzymes have attracted considerable attention in the recent years.

The mechanism behind endonuclease-based genome editing generally requires a first step of DNA single or double strand break, which can then trigger two distinct cellular mechanisms for DNA repair, which can be exploited for DNA editing: the error-prone nonhomologous end-joining (NHEJ) and the high-fidelity homology-directed repair (HDR).

DNA repair through NHEJ frequently generates insertions or deletions (indels), which can alter the frameshift of a coding sequence, thus resulting in gene inactivation. In HDR, a donor nucleic acid co-introduced into the cells functions as a template for precise repair: through appropriate design of the donor nucleic acid, this mechanism can be used to generate a wide range of genetic modifications, including specific mutations of few nucleotides or the insertion of an entire gene.

Endonucleases for gene editing have come in various forms, which includes Clustered Regularly Interspaced Short Palindromic Repeats (CRISPR)/CRISPR associated (Cas) (CRISPR/Cas) systems, Argonaute nucleases (Ago), mega nucleases (MN), zinc finger nucleases (ZFN), and transcription activator-like effector nucleases (TALEN).

Yet, those DNA editing tools, which are based on protein-DNA recognition, tend to suffer (to varying degrees) from multiple drawbacks:
(i) they may lack flexibility and/or are not easy-to-use;
(ii) they may induce off-target DNA cleavage;
(iii) the efficiency of DNA editing may vary substantially; and
(iv) they may not be compatible with modifications that have a negative impact on cell growth.

One of the consequences of such drawbacks is the requirement to further select individual clones in which the HDR event has occurred.

The CRISPR/Cas9 system has been described in U.S. Pat. No. 8,697,359 B1 and US 2014/0068797 A1. Originally an adaptive immune system in prokaryotes (Barrangou and Marraffini, 2014), CRISPR has been recently engineered into a new powerful tool for genome editing.

This engineered system is usually composed of a Cas9 nuclease, in particular the Cas9 nuclease from *S. pyogenes*, and a short RNA sequence, the single-guide (or system-guide) RNA (sgRNA). When co-expressed in the cells, Cas9 and the sgRNA form a complex that specifically recognizes a particular DNA sequence through Watson-Crick pairing and promotes its cleavage. The sgRNA can be designed to match any genomic sequence, the only constraint being the need for the target sequence to be followed by a particular DNA motif, the protospacer adjacent motif (PAM), which corresponds to 5'-NGG for *S. Pyogenes* Cas9 (Doudna and Charpentier, 2014; Hsu et al., 2014).

Compared to other DNA editing tools, including zinc finger nucleases and transcription activator-like effector nucleases, which are based on protein-DNA recognition, the CRISPR/Cas9 technology is remarkably more flexible and easy-to-use. Among the various applications described so far, CRISPR/Cas9 has been implemented in genome-wide functional screenings cultured cells, as well as for the generation of genetically modified organisms or new cancer models.

However, despite the undeniable potential of this new technology, the typical strategies based on CRISPR/Cas9 still bear at least some of the above-mentioned drawbacks:
first, this system can also tolerate a few mismatches between the sgRNA and its target sequence, which can still result in off-target DNA cleavage. While tools have been designed to identify in silico such potential off-target sequences, occasional minor shifts in the secondary structure of the RNA-DNA duplex have been recently reported that could make such predictions more difficult;
secondly, the efficiency of CRISPR/Cas9-mediated DNA editing can vary substantially, depending on the cell model, the sgRNA and the targeted DNA, so that in a given experiment only a fraction of cells within a population will contain the desired genetic modification;
besides the potential issues related to clonal variability, this approach still requires a reasonably high efficiency of CRISPR-mediated editing, and it is obviously still not compatible with modifications that have a negative impact on cell growth.

In particular, the typical design of a cell culture study based on endonuclease technology, including CRISPR/Cas9 technology, still requires the derivation and amplification of clones, and it is therefore constrained by the variable efficiency of DNA-editing and the potential non-specific effects.

Hence, the derivation and the subsequent analysis of a variable number of individual clones still represents an almost inevitable step that is time-consuming and less ameneable to high-throughput technology.

Thus, there remains a need to provide novel tools, methods and uses for improving DNA editing, most preferably in eukaryotic cells, and limit or prevent its drawbacks.

In particular, there remains a need to overcome the drawbacks associated with endonucleases prone to off-target DNA cleavage, such as in CRISPR/Cas systems.

There also remains a need to prevent clonal variability and/or to limit the need for derivation and amplification of clones.

There also remains a need for DNA-editing techniques which are more ameneable to high-throughput technology.

SUMMARY OF THE INVENTION

The invention relates to a method for labeling endonuclease-treated cells, most preferably eukaryotic cells, comprising the steps of:
  a) providing cells or a composition comprising cells;
  b) bringing into contact said cells or said composition with:
    at least one endonuclease suitable for targeting a genomic region of interest in said cells, or a vector suitable for expressing said endonuclease in said cells;
    at least one first nucleic acid suitable for introducing one or more silent mutation(s) in said genomic region by HDR, and optionally one or more non-silent mutation(s); and
    at least one second nucleic acid suitable for introducing one or more silent mutation(s) in said genomic region, but distinct from the silent mutations of the first nucleic acid;
  thereby labeling endonuclease-treated cells.

The invention also relates to a method for detecting a population of endonuclease-treated cells, most preferably eukaryotic cells, comprising the steps of:
  a) providing at least:
    a first population of endonuclease-treated cells comprising one or more silent mutation(s) (and optionally one or more non-silent mutation(s)) introduced in a genomic region of interest by HDR, thereby providing a first signature; and
    a second population of endonuclease-treated cells, comprising one or more silent mutation(s) introduced in the same genomic region of interest by HDR, wherein said silent mutation(s) are distinct from the silent mutation(s) of the first population, thereby providing a second signature;
  b) determining said first and second signature; and
  c) comparing said first and second signature, thereby detecting said first population of endonuclease-treated cells.

The invention also relates to a composition comprising at least:
  (i) a first population of endonuclease-treated cells, comprising one or more silent mutation(s) in a genomic region of interest; and
  (ii) a second population of endonuclease-treated cells, comprising one or more silent mutation(s) in said genomic region, but distinct from the silent mutations of the first population;
  wherein the silent mutation(s) is/are introduced in said cells by HDR after treatment with a same endonuclease targeting the said genomic region of interest.

According to some preferred embodiments, said cells are eukaryotic cells.

The invention also relates to a kit for detecting a population of endonuclease-treated cells comprising at least:
  a first part comprising a first population of endonuclease-treated cells as defined above; and
  a second part comprising a second population of endonuclease-treated cells as defined above.

The invention also relates to a kit for labeling Clustered Regularly Interspaced Short Palindromic Repeats (CRISPR)/CRISPR associated (Cas) (CRISPR/Cas) system-treated cells, comprising:
  (i) at least one CRISPR/Cas system comprising:
    a) a first regulatory element operable in a cell operably linked to at least one nucleotide sequence encoding a CRISPR-Cas system guide RNA that hybridizes with a target genomic region of interest of said cell, and
    b) a second regulatory element operable in said cell operably linked to a nucleotide sequence encoding a Cas endonuclease, wherein components (a) and (b) are located on same or different vectors of the system;
  (ii) at least one nucleic acid suitable for introducing silent mutation(s) in the genomic region of interest of said cell by HDR, and optionally one or more non-silent mutation(s) in said genomic region of interest.

According to some preferred embodiments, said cells are eukaryotic cells.

B. Schematic representation of the CRISPR-barcoding approach to assess the effects of APC restoration on Wnt signaling activation.

C. qPCR analysis from genomic DNA to assess the relative proportion of the APC-WT and APC-STOP barcodes in the different DLD-1 cell subpopulations sorted by FACS. The results correspond to the mean values of the APC-WT to APC-STOP ratio (±SEM; n=3) of one representative of three independent experiments. The asterisk indicates statistical difference (p<0.01 Student's t test). From left to right: Unsorted cells, $GFP^{lo}$ (lowest GFP level) and $GFP^{hi}$ (highest GFP level). The y-axis indicates a normalized WT/STOP ratio.

D. Schematic representation of the experimental procedure to investigate the effects of APC restoration on DLD-1 cell growth through CRISPR-barcoding E. qPCR analysis to assess the relative proportion of the APC-WT and APC-STOP barcodes from DLD-1 cell genomic DNA at the indicated time points as described in (D). The results correspond to the mean values of the APC-WT to APC-STOP ratio of one representative of three independent experiments. «a», «b», «c» and «d», curves represent a variation of the normalized WT/STOP ratio over time (Tref; day 7, day 14, day 21, day 27) in four distinct flasks.

F. Deep sequencing analysis of the «c» genomic DNA samples used in panel (E). The percentage of parental reads (y-axis) containing the APC-WT (WT) and APC-STOP (STOP) barcodes compared to the endogenous sequence is shown over time, (Tref; day 7, day 14, day 21, day 27).

Figure 2:
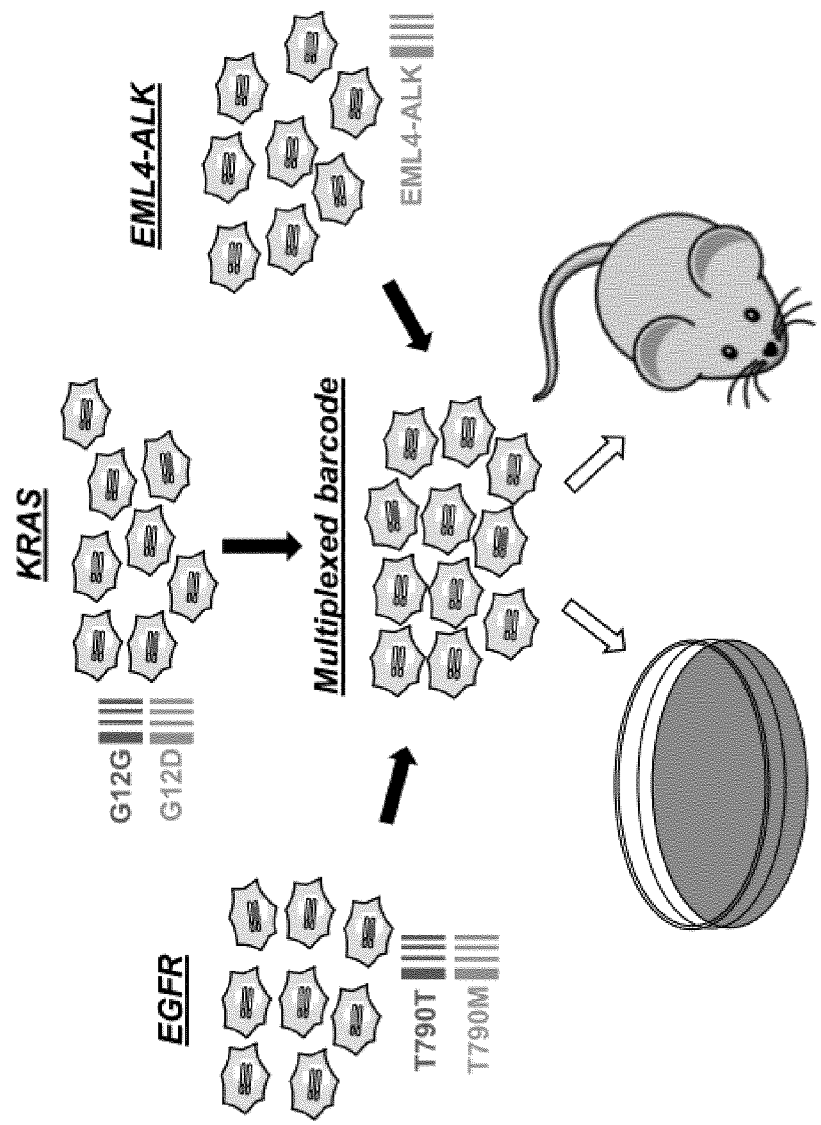

FIG. 2: Schematic representation of multiplexed CRISPR-barcoding in PC9 cells for in vitro or in vivo studies. EGFR-T790M, KRAS-G12D and EML4-ALK are mutations conferring resistance to EGFR inhibition, and are co-introduced in a cell culture in order to obtain a mix of genetically labeled cell subpopulations.

Figure 3:
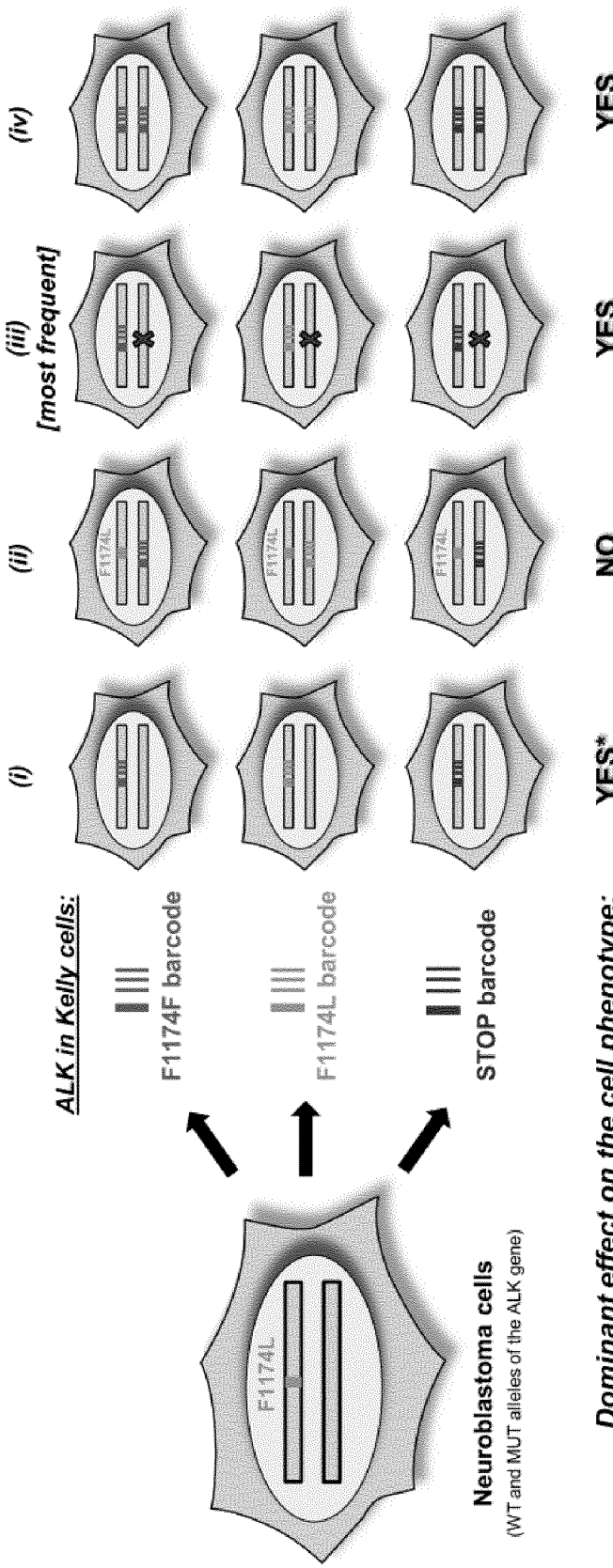

FIG. 3: Schematic for the Repair of ALK F1174L Oncogenic Mutation in Neuroblastoma cells. The incorporation of each exogenous sequence can result in four possible combinations: for three of them, including the probably most frequent barcode/indel, the phenotypically dominant sequence expressed in the cell is expected to be the one encoded by the barcode.

Figure 4:
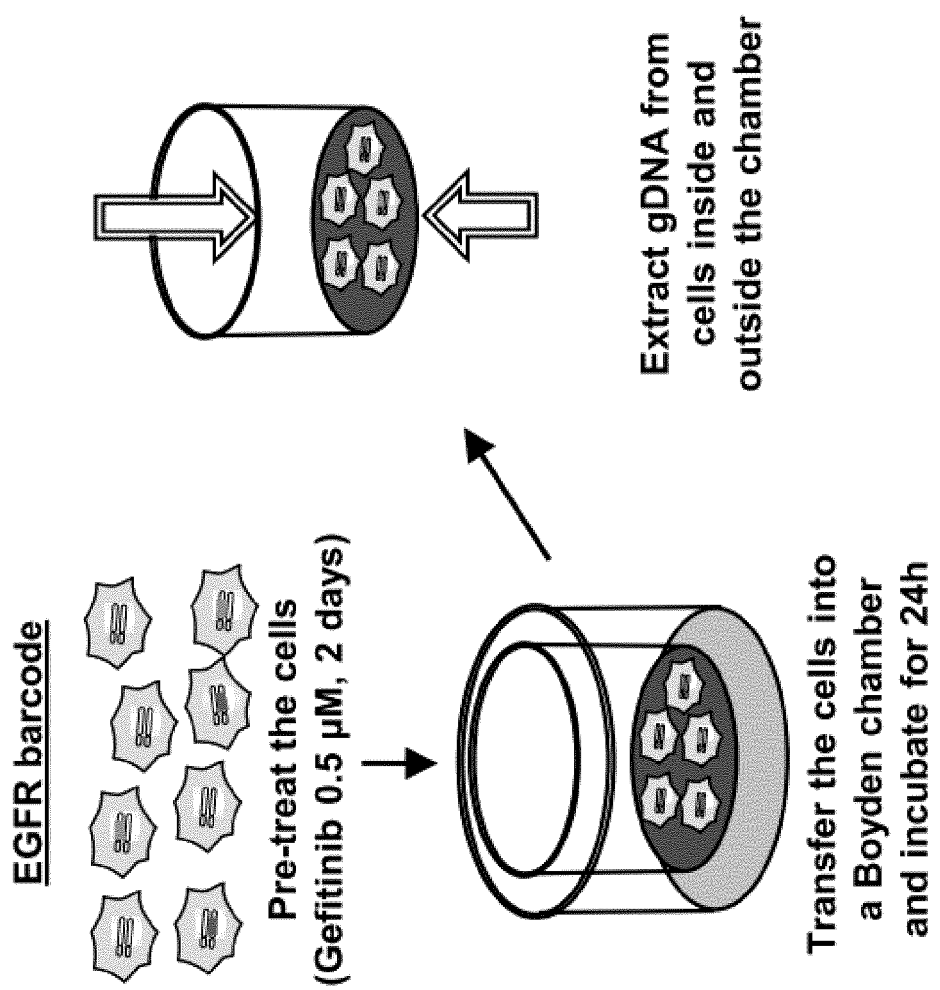

FIG. 4: Schematic for assessing cell invasion and migration using CRISPR barcoding. EGFR-barcoded PC9 cells were pre-treated for two days with gefitinib, then transferred to Boyden chambers containing matrigel.

Figure 5:
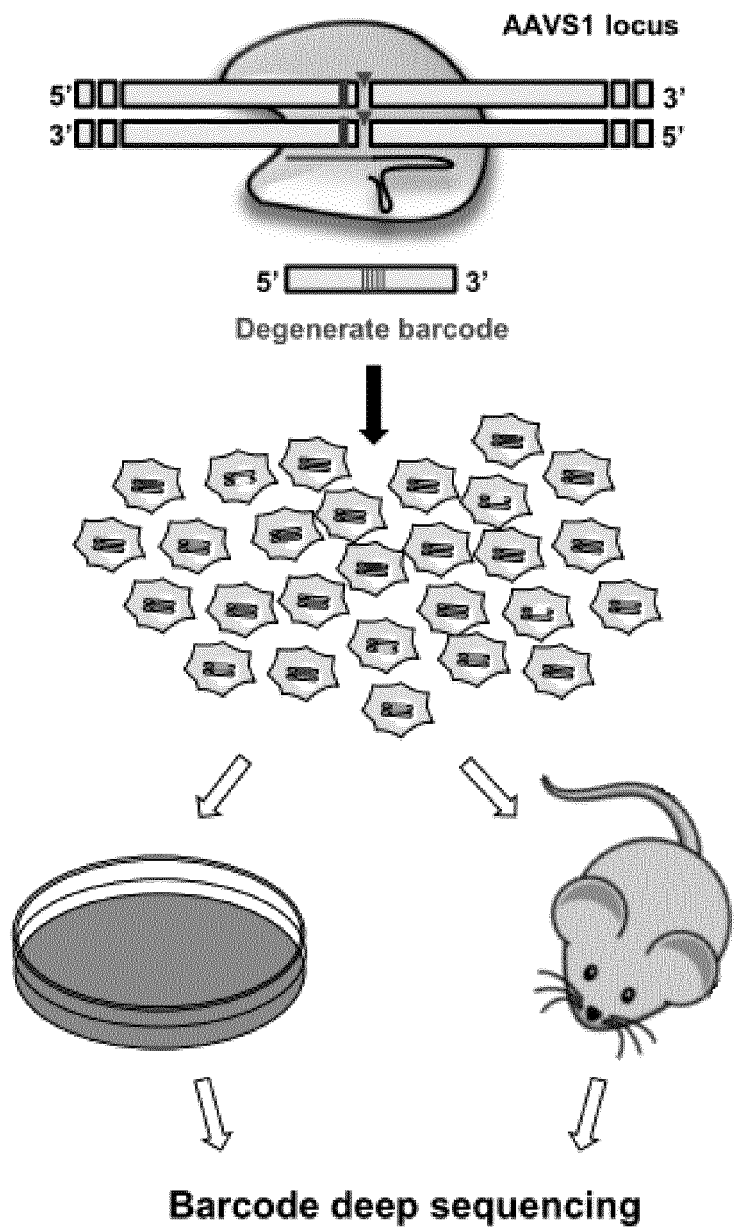

FIG. 5: Schematic for probing Intratumor Heterogeneity using Degenerate CRISPR-Barcodes. Cells are sequentially transfected for CRISPR-barcoding with two distinct sgRNAs, and a degenerate ssODN containing a SalI restriction site is used to allow RFLP quantification of the fraction of cells containing a genetic label. After barcoding, part of the cells is bilaterally injected in the fat pad of immunocompromised mice, while the rest is maintained in culture. At different time-points, the mice are sacrificed and gDNA is derived from both the tumors and the cells in culture.

Figure 6:
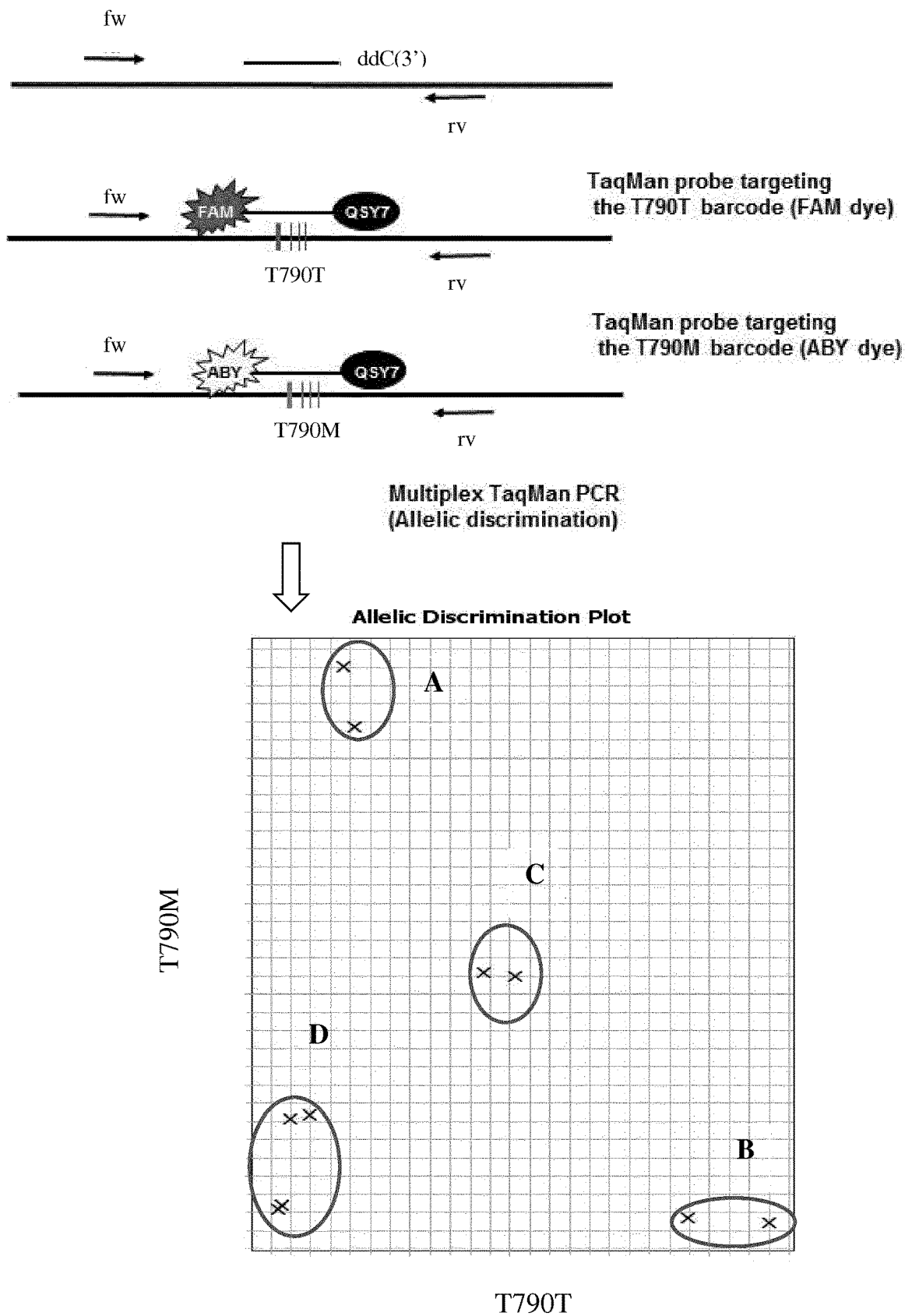

FIG. 6: Schematic for TaqMan multiplex detection of genomic barcodes. TaqMan PCR was performed from gDNA derived from PC9 cells transfected for EGFR-T790 CRISPR-barcoding using a couple of unmodified forward (fw) and reverse primers (rv), together with a TaqMan probe targeting the T790T barcode (FAM dye) and a TaqMan probe targeting the T790M barcode (ABY dye). To limit amplification of the endogenous sequence, a specific blocking oligonucleotide, containing phosphorothioate bonds and a ddC in 3', was added to the reaction. A typical allelic discrimination plot obtained from a set of representative samples is shown with: A. samples containing a subpopulation of cells barcoded with T790M; B. samples containing a subpopulation of cells barcoded with T790T; C. samples containing two subpopulations of cells barcoded with T790M and T790T; D. cells without barcode (negative control); (y-axis represents the T790M allele and x-axis represents the T790T allele).

DETAILED DESCRIPTION OF THE INVENTION

Methods, uses, compositions and kits described herein all relate to the concept of labeling specifically endonuclease-treated cells, most preferably eukaryotic cells, in which a given recombination event has occurred.

In order to counteract the drawbacks that hinder endonuclease-based DNA editing, we have thus devised an endonuclease-based "barcoding" protocol, a strategy in which a potentially functional modification in a genomic region of interest is coupled with a series of silent (i.e. point) mutations, functioning as a genetic label for cell tracking.

In parallel, a second barcode comprising or consisting of distinct silent mutation(s) is inserted and used as a control for off-target effects (i.e. CRISPR off-target cleavage). The genomic DNA from the resulting mixture of modified and unmodified cells is then able to establish a characteristic signature, which can be determined and compared (i.e. using primers complementary to the said signature of the populations of eukaryotic cells in order to assess the relative proportion of each barcode).

Of note, the second barcode comprises distinct silent mutation(s), which may thus encompass embodiments wherein:
  all the silent mutation(s) from the second barcode are on different positions of the genomic region of interest compared to the first barcode;
  at least some of the silent mutation(s) from the second barcode are on different positions of the genomic region of interest compared to the first barcode;
  when silent mutation(s) from the second barcode are on the same positions of the genomic region if interest compared to the first barcode, they are preferably distinct.

Advantageously, a number of distinct barcodes may thus be generated after homology-directed repair (HDR).

Also advantageously, the barcoding approach does not require particularly high levels of DNA editing.

Although those methods, uses, compositions and kits are particularly useful in CRISPR-based DNA editing of eukaryotic cells, they may also be applied to other non-eukaryotic cells and/or endonucleases, including other endonucleases prone to off-target DNA cleavage, and/or which involve homology-directed repair (HDR) in said cells.

Endonucleases which are particularly considered include nucleic acid-guided nucleases, in particular DNA-guided DNA nucleases and RNA-guided DNA nucleases, especially Type II CRISPR-Cas endonucleases.

As illustrated herein and in the examples, two distinct endonuclease-barcodes (in that case CRISPR-barcodes) were coupled to a particular missense/nonsense mutation and to its silent counterpart, which we used as a control for potential CRISPR/Cas9 off-target cleavage. Using specific primers for real-time quantitative PCR (qPCR), we could assess how the fraction of cells containing each barcode varied within a heterogeneous population following exposure to a particular selective condition, which depended on the cell model used. We applied this strategy to manipulate the endogenous sequence of different oncogenes and tumor suppressors in various cancer cell models, and we assessed the effects of such modifications on signaling pathway activation, cell growth and invasion, or resistance to chemotherapy, both in vitro and in vivo.

Hence, by exposing the cells to a given selective condition, this approach can be used to functionally characterize the effects of different types of mutations of a particular gene of interest.

Also, the incorporation of a genetic barcode in the genome of the cells allows their tracking within a heterogeneous population of endonuclease-modified and unmodified cells, and circumvents the need for clonal selection.

The introduction of silent mutation(s) in distinct barcodes further has the advantage of preventing, or reducing the likelihood of, the recombinant sequence to be cleaved by the endonuclease and, if applicable, its single-guide nucleic acid, such as a sgRNA (i.e. for CRISPR/Cas systems).

As a proof-of-concept of our strategy, we repaired the mutated sequence of the tumor suppressor APC in colorectal cancer cells using CRISPR-barcoding, and showed that adenomatous polyposis coli (APC) restoration resulted in the inhibition of both Wnt signaling reporter activity and cell growth. The tumor suppressor gene APC is a major component of the destruction complex that promotes the degradation of free β-catenin. Indeed, more than 80% of colorectal cancers contain alterations of the APC gene, generally corresponding to nonsense or frameshift mutations, resulting in the expression of truncated and inactive proteins To further illustrate the wide range of potential applications of this approach, we used CRISPR-barcoding to modify the sequence of other cancer-related genes, including TP53, ALK, EGFR and KRAS, in various tumor cells, and we assessed the effects of such alterations on cell growth, invasion and resistance to chemotherapy, both in vitro and in vivo. Thus, by preventing the limitations associated with the low efficiency and the potential off-target effects of DNA editing, our studies demonstrate that endonuclease-barcoding, in particular CRISPR-barcoding, is a fast, convenient and effective strategy to investigate the functional consequences of a particular genetic modification in cells, including eukaryotic and non-eukaryotic cells, and most preferably in eukaryotic cells.

DEFINITIONS

The terms «at least one» and «one or more» are used interchangeably. Accordingly, the term «at least one» may comprise «two or more», «three or more», «four or more», «five or more», and so on.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Nuclease" and "endonuclease" are used interchangeably herein to mean one or more enzymes or enzyme-containing complexes (which may include, if applicable, protein-nucleic acid complexes such as Cas9 in complex with sgRNAs) which possesses catalytic activity for polynucleotide cleavage, in particular DNA cleavage. Endonucleases which are considered include naturally occurring, non-naturally occurring, recombinant, chimeric and/or heterologous endonucleases, and analogs thereof.

Analogs of endonucleases may include endonucleases which share at least 80% of sequence identity with a given endonuclease, which includes at least 80%; 85%; 90% and 95% of identity, based on an optimum alignment.

The optimum alignment of the sequences for the comparison can be carried out by computer using known algorithms Entirely preferably, the percentage sequence identity is determined using the CLUSTAL W2 software (version 2.1), the parameters being fixed as «default». By "endonuclease suitable for targeting a genomic region of interest" it is meant any endonuclease, as described above, that is able to target specifically a genomic region of interest of a given cell, and to provide catalytic activity for polynucleotide cleavage on the targeted genomic region.

Thus, said definition may include both:

(i) endonucleases having at least one targeting domain and at least one active domain for polynucleotide cleavage; and/or (ii) endonuclease having at least one active domain for polynucleotide cleavage, wherein the targeting domain is part of a distinct polypeptide and/or a distinct polynucleotide.

In general, "CRISPR system" or «CRISPR/Cas system» refers collectively to transcripts and other elements involved in the expression of or directing the activity of CRISPR-associated ("Cas") genes, including sequences encoding one or more of: a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous. CRISPR system), a guide sequence (also referred to as a "spacer" in the context of an endogenous CRISPR system), a single-guide nucleic acid (in particular a single-guide RNA (sgRNA)) or other associated sequences and transcripts from a CRISPR locus needed for targeting a genomic region of interest.

Examples of "CRISPR system" which are considered by the invention include Type II (or "class 2") CRISPR systems such as CRISPR/Cas9 or the more recently characterized CRISPR from Provotella and *Francisella* 1 (Cpf1) in Zetsche et al. ("Cpf1 is a Single RNA-guided Endonuclease of a Class 2 CRISPR-Cas System (2015); Cell; 163, 1-13).

By "cleavage domain" or "active domain" or "nuclease domain" of a nuclease/endonuclease it is meant the polypeptide sequence or domain within the nuclease which possesses the catalytic activity for polynucleotide cleavage, in particular DNA cleavage. A cleavage domain can be contained in a single polypeptide chain or cleavage activity can result from the association of two (or more) polypeptides. A single nuclease domain may consist of more than one isolated stretch of amino acids within a given polypeptide.

By "recombination" it is meant a process of exchange of genetic information between two polynucleotides. As used herein, "homology-directed repair (HDR)" refers to the specialized form DNA repair that takes Place, for example, during repair of double-strand breaks in cells. This process requires nucleotide sequence homology, uses a "donor" molecule to template repair of a "target" molecule (i.e., the one that experienced the double-strand break), and leads to the transfer of genetic information from the donor to the target. Homology-directed repair may result in an alteration of the sequence of the target molecule (e.g., insertion, deletion, mutation), if the donor polynucleotide differs from the target molecule and part or all of the sequence of the donor polynucleotide is incorporated into the target DNA. In some embodiments, the donor polynucleotide, a portion of the donor polynucleotide, a copy of the donor polynucleotide, or a portion of a copy of the donor polynucleotide integrates into the target genomic region of interest.

By "non-homologous end joining (NHEJ)" it is meant the repair of double-strand breaks in DNA by direct ligation of the break ends to one another without the need for a homologous template (in contrast to homology-directed repair, which requires a homologous sequence to guide repair). NHEJ often results in the insertion or deletion (indel) of one or more nucleotides near the site of the double-strand break.

"Complementarily" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%; 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self 17 hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 8 or 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides).

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

«Locus of interest» and «genomic region of interest» are used interchangeably herein to mean the region of the genome for which HDR must occur. When HDR requires a «donor» nucleic acid, the genomic region of interest can be defined as the region that is complementary to the «donor» nucleic acid.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a, coding sequence if the promoter affects its transcription or expression.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

By «silent mutation» it is meant mutations which, when introduced into the genomic region of interest, do not alter the phenotype of the cell and/or organism in which they occur. Silent mutations can occur in non-coding regions (outside of genes or within introns), or they may occur within exons. When silent mutations occur within exons, they either do not result in a change to the amino acid sequence of a protein, or result in the insertion of an alternative amino acid with similar properties to that of the original amino acid. Yet, according to a most preferred embodiment of the invention, «silent mutations» consist of mutations which occur within an exon or open-reading frame but that do not result in a change to the amino acid sequence of the protein, or fragment thereof, corresponding to said exon or open-reading frame. Examples of silent mutations include mutations introducing restriction site(s) recognized by one or more endonucleases, but that do not alter the phenotype of the cell and/or organism.

Accordingly, «non-silent mutations» preferably consist of mutations which occur within an exon and that do result in a change to the amino acid sequence of the protein, or fragment thereof, corresponding to said exon. Said change may include deletions, substitutions and insertions of another amino acid sequence. Examples of non-silent mutations include mutations introducing a STOP codon within an open reading frame (ORF).

A «cell» is selected from the group consisting of eukaryotic and non-eukaryotic cells; which includes eukaryotic cells, and prokaryotic cells selected from bacteria, and archaebacterias.

An «eukaryotic cell» may be selected from the group comprising or consisting of: a yeast, an eukaryotic single-cell organism, a somatic cell, a germ cell, a stem cell, a plant cell, an algal cell, an animal cell, in invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, and a human cell. Examples of eukaryotic, cells which are specifically considered by the invention include PC9 (lung cancer) cells, BT474 and MCF7 (breast cancer) cells, and DLD-1 and HCT116 (colon cancer) cells.

The term "naturally-occurring" or "unmodified" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "chimeric" as used herein as applied to a nucleic acid or polypeptide refers to two components that are defined by structures derived from different sources. For example, where "chimeric" is used in the context of a chimeric polypeptide (e.g., a chimeric Cas9/Csn1 protein), the chimeric polypeptide includes amino acid sequences that are derived from different polypeptides. A chimeric polypeptide may comprise either modified or naturally-occurring polypeptide sequences (e.g., a first amino acid sequence from a modified or unmodified Cas9/Csn1 protein; and a second amino acid sequence other than the Cas9/Csn1 protein). Similarly, "chimeric" in the context of a polynucleotide encoding a chimeric polypeptide includes nucleotide sequences derived from different coding regions (e.g., a first nucleotide sequence encoding a modified or unmodified Cas9/Csn1 protein; and a second nucleotide sequence encoding a polypeptide other than a Cas9/Csn1 protein).

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

"Heterologous," as used herein, means a nucleotide or polypeptide sequence that is not found in the native nucleic acid or protein, respectively. For example, in a chimeric Cas9/Csn1 protein, the RNA-binding domain of a naturally-occurring bacterial Cas9/Csn1 polypeptide (or a variant thereof) may be fused to a heterologous polypeptide sequence (i.e. polypeptide sequence from a protein other than Cas9/Csn1 or a polypeptide sequence from another organism). The heterologous polypeptide sequence may exhibit an activity (e.g., enzymatic activity) that will also be exhibited by the chimeric Cas9/Csn1 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 site-directed polypeptide, a variant Cas9 site-directed polypeptide may be fused to a heterologous polypeptide (i.e. a polypeptide other than Cas9), which exhibits an activity that, will also be exhibited by the fusion variant Cas9 site-directed polypeptide. A heterologous nucleic acid sequence may be linked to a variant Cas9 site-directed polypeptide (e.g., by genetic engineering) to generate a nucleotide sequence encoding a fusion variant Cas9 site-directed polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., DNA-targeting RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

In particular, the term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol II promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Methods for Detecting & Labeling Cells

According to a first object, the invention relates to a method for labeling endonuclease-treated cells, most preferably eukaryotic cells, comprising the steps of:

a) providing cells or a composition comprising cells;

b) bringing into contact said cells or said composition with:

at least one endonuclease suitable for targeting a genomic region of interest in said cells, or a vector suitable for expressing said endonuclease in said cells;

at least one first nucleic acid suitable for introducing one or more silent mutation(s) in said genomic region by HDR, and optionally one or more non-silent mutation(s) in said genomic region of interest; and at least one second nucleic acid suitable for introducing one or more silent mutation(s) in said genomic region, but distinct from the silent mutations of the first nucleic acid;

thereby labeling endonuclease-treated cells.

The first and second nucleic acid are considered as «donor» nucleic acids. In step b), they are thus able to integrate into the target genomic region of interest by HDR.

The step b) of bringing into contact said cells with said first and second nucleic acid is achieved in the same composition, or in different compositions ("in parallel") before mixing, thereby providing labeled (or "barcoded") endonuclease-treated cells.

When the first and second nucleic acid are brought into contact with said cells in a same composition, the first and second nucleic acid can be brought into contact either simultaneously or sequentially (one after the other).

When the first and second nucleic acid are brought into contact with said cells in a different composition, the first and second nucleic acid are brought into contact in parallel. Accordingly, the at least first nucleic acid is brought into contact with one or more cells in a first composition, and the at least second nucleic acid is brought into contact with one or more cells in a second composition; the first and second composition are then mixed up, thereby labeling endonuclease-treated cells (i.e. see FIG. 1B).

According to some embodiments, the first and second nucleic acid are brought into contact with said cells in a manner suitable for the HDR event to occur simultaneously.

According to other embodiments, the first and second nucleic acid are brought into contact with said cells in a manner suitable for the HDR event to occur sequentially or in parallel.

One advantage for bringing said nucleic acids into contact with said cells in a sequential manner or in parallel, is to prevent, or reduce the likelihood of the incorporation of the donor nucleic acids into different alleles of the same cell.

Another advantage is to improve transfection efficiency.

Accordingly, the said first and second nucleic acids (which are most preferably from the same type) can be selected from a group comprising or consisting of: single-stranded deoxyribonucleotide(s) (ssDNA); double-stranded deoxyribonucleotide(s) (dsDNA); single-stranded ribonucleotide(s) (ssRNA); double-stranded ribonucleotide(s) (dsRNA); single-stranded oligo-deoxyribonucleotide(s) (ssODNA); double-stranded oligo-deoxyribonucleotide(s) (dsODNA); single-stranded oligo-ribonucleotide(s) (ssORNA); double-stranded oligo-ribonucleotide(s) (dsORNA); RNA-DNA duplexes; either in a modified or non-modified form. When the said nucleic acids are in a modified form, they may optionally comprise degenerate sequences and non-standard bases.

For instance, the use of a ssODNA as a donor nucleic acid has been described in: Chen et al. (2011). High-frequency genome editing using ssDNA oligonucleotides with zinc-finger nucleases. *Nat Methods*. 8(9):753-5.

In a non-limitative manner, said nucleic acids may be in the form of messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers.

According to a preferred embodiment, the said nucleic acids are deoxyribonucleic acids.

They may be of varying length depending on the nature and length of the genomic region of intest and also for achieving hybridization in the cell and HDR after endonuclease treatment. They may thus comprise or consist of 8, 9, 10, 11, 12, 13, 14, 15, 16, 17, 18, 19, 20, 21, 22, 23, 24, 25, 30, 35, 40, 45, 50, 100, 150 or more nucleotides.

When the nucleic acid(s) is/are used for introducing silent mutation(s) in the said genomic region of interest, they may be single-stranded oligo-deoxyribonucleotide(s) (ssODNA). When the nucleic acid(s) is/are used for the introduction or replacement of a longer nucleic acid sequence by HDR (i.e. a complete gene), they may be double-stranded deoxyribonucleotide(s) (dsDNA).

When the said first and second donor nucleic acids are double-stranded nucleic acids, they may either comprise blunt or sticky ends.

According to one embodiment, the said first and second donor nucleic acids comprise blunt ends.

According to one embodiment, the first and second nucleic acid are single-stranded oligo-deoxyribonucleotide(s) (ssODNA).

According to one more particular embodiment, the first and second nucleic acid are single-stranded oligo-deoxyribonucleotide(s) (ssODNA) or blunt-ended double-stranded oligo-deoxyribonucleotide(s) (dsODNA).

Yet, more than one type of "barcode" may be present within a same sample (i.e. a composition or tissue). Accordingly, the HDR events associated with the introduction of each "barcode" may occur either in the same sample, or in distinct samples which may then be mixed together in order to form one single sample comprising a mixture of said cells, thereby providing a mixture of labeled endonuclease-treated cells (i.e. see FIG. 2).

Advantageously, the barcode corresponding to each cell population can then be detected, for instance by Multiplex TaqMan PCR.

Endonucleases that are suitable for the invention include any endonuclease suitable for introducing, after sequence-specific cleavage of the genomic region of interest, a donor nucleic acid, or fragment thereof, by HDR.

Examples of such endonucleases are known in the Art.

According to one particular embodiment, said endonuclease is selected from a group consisting of: a Clustered Regularly Interspaced Short Palindromic Repeats (CRISPR)-CRISPR associated (Cas) (CRISPR-Cas) endonuclease, an Argonaute nuclease (Ago), a mega nuclease (MN), a zinc finger nuclease (ZFN), and a transcription activator-like effector nuclease (TALEN); and preferably is a CRISPR-Cas endonuclease.

A CRISPR-Cas endonuclease may be selected from Cas9 or Cpf1, and preferably is a Cas9 endonuclease.

Accordingly, said vector is preferably a CRISPR-Cas system, such as a CRISPR-Cas 9 system.

A MN, also called "homing endonuclease", belongs to a class of highly sequence-specific and efficient enzymes that were first discovered in yeast, but are widely expressed in different species (i.e. the LAGLIDADG Homing Endonuclease Family). MN can induce site-specific double-strand breaks and thereby stimulate homologous recombination. Naturally occurring MNs have been engineered to specifically target and edit particular genomic loci in a variety of cell types and organisms. In a non-limitative manner, MNs which are suitable for the invention have been reported (Grizot et al. (2010). Generation of redesigned homing endonucleases comprising DNA-binding domains derived from two different scaffolds. *Nucleic Acids Res* 38(6) 2006-18; Chevalier B S et al. (2002). Design, activity, and structure of a highly specific artificial endonuclease. *Mol Cell.* 10(4):895-905; Gao H et al. (2010). Heritable targeted mutagenesis in maize using a designed endonuclease. *Plant J.* 61(1):176-87; Fernández-Martínez L T et al. (2014). Use of the meganuclease I-SceI of *Saccharomyces cerevisiae* to select for gene deletions in actinomycetes. *Sci Rep.* 4:7100; Bernardini F et al. (2014). Site-specific genetic engineering of the *Anopheles gambiae* Y chromosome. *Proc Natl Acad Sci USA.* 111(21):7600-5; Popplewell L et al. (2013). Gene correction of a duchenne muscular dystrophy mutation by meganuclease-enhanced exon knock-in. *Hum Gene Ther.* 24(7):692-701; Marcaida M J et al. (2008). Crystal structure of I-DmoI in complex with its target DNA provides new insights into meganuclease engineering. Proc Natl Acad Sci USA. 105(44):16888-93; Ogino H et al. (2006) High-throughput transgenesis in *Xenopus* using I-SceI meganuclease. *Nat Protoc.* 1(4):1703-10; Arnould S et al. (2011) The I-CreI meganuclease and its engineered derivatives: applications from cell modification to gene therapy. *Protein Eng Des Sel.* 24(1-2):27-31.

A ZFN includes a zinc finger domain with specific binding affinity for a desired specific target sequence. There are a large number of naturally occurring zinc finger DNA binding proteins which contain zinc finger domains that may be incorporated into a ZFN designed to bind to a specific endogenous chromosomal sequence.

In a non-limitative manner, ZFN and vectors which are suitable for the invention are described in EP 2368982 A2.

Zinc finger nucleases suitable for the invention are also reported in: Foley J E et al. (2009). Targeted mutagenesis in zebrafish using customized zinc-finger nucleases. *Nat Protoc.* 1855-67; Wright D A et al. (2006) Standardized reagents and protocols for engineering zinc finger nucleases by modular assembly. *Nat Protoc.* 1(3):1637-52.; Maeder M L et al. (2009) Oligomerized pool engineering (OPEN): an 'open-source' protocol for making customized zinc-finger arrays. *Nat Protoc.;* 4(10): 1471-501; Sander J D et al. (2011). Selection-free zinc-finger-nuclease engineering by context-dependent assembly (CoDA). *Nat Methods.* 8(1): 67-9; Bae, K. H. (2003) Human zinc fingers as building blocks in the construction of artificial transcription factors *Nat Biotechnol* 21, 275-80.; Beerli, R. R. & Barbas, C. F., (2002) Engineering polydactyl zinc-finger transcription factors *Nat Biotechnol* 0.20, 135-41.; Carroll D. et al (2006) Design, construction and in vitro testing of zinc finger nucleases *Nature Protocols* 1: 1329-1341.; Greisman, H. A. & Pabo, C. O. (1997) A general strategy for selecting high-affinity zinc finger proteins for diverse DNA target sites *Science* 275, 657-61.; Hurt, J. A., et al. (2003) Highly specific zinc finger proteins obtained by directed domain shuffling and cell-based selection *Proc Natl Acad Sci USA* 100, 12271-6.; Jamieson, A. et al. (2003) Drug Discovery with Engineered Zinc-Finger Proteins *Nature Reviews Drug Discovery* 2, 361-368.

A "Transcriptional Activator-Like Element Nuclease," (TALEN) as used herein, refers to an artificial nuclease comprising a transcriptional activator like effector DNA binding domain to a DNA cleavage domain, for example, a FokI domain.

In a non-limitative manner, a number of modular assembly schemes for generating engineered TALE constructs have been reported (Zhang, F. et. al. (2011). "Efficient construction of sequence-specific TAL effectors for modulating mammalian transcription". *Nature Biotechnology* 29 (2):149-53; Geißler, R.; et al. (2011), Shiu, Shin-Han. ed. "Transcriptional Activators of Human Genes with Programmable DNA-Specificity". *PLoS ONE* 6 (5): e19509; Cermak, T.; et al. (2011). "Efficient design and assembly of custom TALEN and other TAL effector-based constructs for DNA targeting". *Nucleic Acids Research*; Morbitzer, R.; et al. (2011). "Assembly of custom TALE-type DNA binding domains by modular cloning". *Nucleic Acids Research*; Li, T. et al. (2011). "Modularly assembled designer TAL effector nucleases for targeted gene knockout and gene replacement in eukaryotes". *Nucleic Acids Research*.; Weber, E.; et al. (2011). Bendahmane, Mohammed. ed. "Assembly of Designer TAL Effectors by Golden Gate Cloning". *PLoS ONE* 6 (5): e19722); Reyon D et al. (2012). FLASH assembly of TALENs for high-throughput genome editing. *Nat Biotechnol.* 30(5):460-5.; Cermak T, et al. (2011). Efficient design and assembly of custom TALEN and other TAL effector-based constructs for DNA targeting. *Nucleic Acids Res.* 39(12); Sander J D, et al. (2011). Targeted gene disruption in somatic zebrafish cells using engineered TAL-ENs. *Nat Biotechnol.* 29(8):697-8; Bogdanove A J, Voytas D R (2011). TAL effectors: customizable proteins for DNA targeting *Science.* 333(6051):1843-6.; Zhang F. et al. (2011). Efficient construction of sequence-specific TAL effectors for modulating mammalian, transcription. Nat Biotechnol. 149-

53; Kim Y et al. (2013). A library of TAL effector nucleases spanning the human genome. *Nat Biotechnol* (3):251-8).

An Argonaute nuclease is a family of endonucleases that uses 5' phosphorylated short single-stranded nucleic acids as guides to cleave targets.

In a non-limitative manner, Argonaute nucleases suitable for the invention are RNA-guided endonucleases or DNA-guided endonucleases as described in Gao et al. (Nature Biotechnology; 34, 768-773; 2016). Accordingly, an Argonaute nuclease suitable for the invention may be a DNA-guided endonuclease such as a *Natronobacterium gregotyi* Argonaute (NgAgo) nuclease.

In some embodiments, one or more elements of a CRISPR system is/are derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides.

Among CRISPR-Cas systems, a type II CRISPR system from *Streptococcus pyogenes* involves only a single gene encoding the Cas9 protein and two RNAs—a mature CRISPR RNA (crRNA) and a partially complementary trans-acting RNA (tracrRNA)—which are necessary and sufficient for RNA-guided silencing of foreign DNAs.

Accordingly, a CRISPR-Cas system of the invention may involve a Cas endonuclease and a CRISPR-Cas system guide nucleic acid, such as a CRISPR-Cas system guide RNA that hybridizes with the target sequence.

Accordingly, a CRISPR-Cas system suitable for the invention may comprise or consist of one or more vectors comprising:

a) a first regulatory element operable in a cell (preferably an eukaryotic cell) operably linked to at least one nucleotide sequence encoding a CRISPR-Cas system guide nucleic acid, such as a CRISPR-Cas system guide RNA, that hybridizes with the target sequence, and b) a second regulatory element operable in a cell (preferably an eukaryotic cell) operably linked to a nucleotide sequence encoding a Cas endonuclease, such as a Type-II Cas9 protein, wherein components (a) and (b) are located on same or different vectors of the system, whereby the guide nucleic acid targets the target sequence and the Cas endonuclease (i.e. Type II-Cas9) protein cleaves the genomic region of interest.

In a non-limitative manner, CRISPR-Cas systems which are suitable for the invention are described in U.S. Pat. No. 8,697,359 B1 and US 2014/0068797 A1, or in Zetsche et al. ("Cpf1 is a Single RNA-guided Endonuclease of a Class 2 CRISPR-Cas System (2015); *Cell;* 163, 1-13).

In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme comprises a detectable marker, such as fluorescent marker. In some embodiments, the CRISPR enzyme is a Cas protein, which includes a Type II-Cas9 protein or one of its isoforms.

Examples of such vectors include lentiviruses and adeno-associated viruses, and types of such vectors can also be selected for targeting particular types of eukaryotic cells. Other examples of expression vectors, including mammalian expression vectors, capable of directing expression of a given nucleic acid in particular cell types are known in the Art.

According to one preferred embodiment of said method, said endonuclease or vector is respectively a Type II-Cas9 endonuclease or a CRISPR-Cas system.

Illustratively and in a non-limitative manner, one example of CRISPR barcoding protocol for eukaryotic cells requires:

a first donor DNA consisting of a ssODNA (ssODN-1), comprising a non-silent mutation to be introduced into the genomic region of interest, and a first set of silent mutations;

a second donor DNA consisting of a ssODNA (ssODN-2), comprising a second set of silent mutations to be introduced into the same genomic region of interest, wherein said silent mutation do not modify the amino acid sequence of the protein encoded by said genomic region; and an expression vector (i.e. a plasmid) for expressing Cas9 and a sgRNA into said eukaryotic cells.

Cells are then transfected with the expression vector and the two or more donor DNAs.

Therefore, a mixed population of eukaryotic cells is produced, comprising at least (i) eukaryotic cells in which no HDR as occurred; (ii) eukaryotic cells in which HDR has occurred in the presence of ssODN-1; (iii) eukaryotic cells in which HDR has occurred in the presence of ssODN-2; and optionally (iv) eukaryotic cells in which the DNA cleavage has been repaired by NHEJ.

The proportion of cells containing either ssODN-1 or ssODN-2 is then determined (preferably by quantitative PCR (qPCR), Restriction Fragment Length Polymorphism (RFLP)-PCR or next-generation sequencing (NGS)), generally 2-3 days after transfection (corresponding to $t_0$), and then repeated over time, which thus provides an indication if the genomic region of interest induces a negative or positive effect on cell growth.

The ssODN-2, which does not introduce modifications into the amino acid sequence, is used as an internal control for normalization, in order to by-pass potential non-specific cleavage associated with CRISPR.

Advantageously, the silent mutations of the first and second signature in said nucleic acids may be further swapped, as a control for potential effects of such silent mutations on mRNA stability and gene expression levels.

The above-mentioned methods for labeling endonuclease-treated cells in a composition may provide, in the said composition, a mixture of modified and unmodified cells. Accordingly, they may provide it least:

a first population of endonuclease-treated cells comprising one or more silent mutation(s) introduced in a genomic region of interest by HDR, thereby providing a first signature; and a second population of endonuclease-treated cells, comprising one or more silent mutation(s) introduced in the same genomic region of interest by HDR, wherein said silent mutation(s) are distinct from the silent mutation(s) of the first population, thereby providing a second signature;

optionally a third population of endonuclease-treated cells, comprising one or more silent mutation(s) introduced in the same genomic region of interest by HDR, wherein said silent mutation(s) are distinct from the silent mutation(s) of the first population and optionally the second population, thereby providing a third signature;

optionally a population of unmodified cells and/or modified cells by NHEJ.

Advantageously said first and second signature can be further used as a marker, for the detection or follow-up of a population of cells, most preferably eukaryotic cells, within a complex mixture (i.e. a composition or a tissue). Otherwise said, they provide a «barcode» for detecting the variation of one population over the others, for instance in the presence of a stimulus, without the need for an additional step of selection or identification of clones.

According to one embodiment, the method for labeling cells, as described above, is used for the preparation of a composition, (i.e. a pharmaceutical composition and/or a medicament), comprising or consisting of at least:
said first population of endonuclease-treated cells; and
said second population of endonuclease-treated cells.

Accordingly, the above-mentioned methods for labeling can be further integrated into methods for detecting a population of endonuclease-treated cells, most preferably eukaryotic cells, in a sample (i.e. a composition or an isolated biological tissue) or an individual (i.e. a human or non-human mammal), as further described here-below.

Examples of compositions or isolated biological tissues which are particularly considered include compositions and tissues comprising or consisting of cancer cell lines.

In vitro methods are particularly considered. Thus, according to a second object, the invention relates to a method for detecting a population of endonuclease-treated cells, most preferably eukaryotic cells, comprising the steps of:
a) providing at least:
a first population of endonuclease-treated cells comprising one or more silent mutation(s) introduced in a genomic region of interest by HDR, thereby providing a first signature; and
a second population of endonuclease-treated cells, comprising one or more silent mutation(s) introduced in the same genomic region of interest by HDR, wherein said silent mutation(s) are distinct from the silent mutation(s) of the first population, thereby providing a second signature;
b) determining said first and second signature; and
c) comparing said first and second signature, thereby detecting said first population of endonuclease-treated cells.

Accordingly, a ratio between said first and second signature, or alternatively a ratio between said second and first signature, provides an indication of the variation of the first population over the second population.

Accordingly, the invention relates to a method for detecting a population of endonuclease-treated cells, most preferably eukaryotic cells, in a sample, comprising the steps of:
a) providing a sample comprising at least:
a first population of endonuclease-treated cells comprising one or more silent mutation(s) introduced in a genomic region of interest by HDR, thereby providing a first signature; and
a second population of endonuclease-treated cells, comprising one or more silent mutation(s) introduced in the same genomic region of interest by HDR, wherein said silent mutation(s) are distinct from the silent mutation(s) of the first population, thereby providing a second signature;
b) determining said first and second signature in said sample; and
c) comparing said first and second signature, thereby detecting said first population of endonuclease-treated cells in said sample;
wherein said sample is preferably selected from the group consisting of a composition (such as a composition described above) or an isolated biological tissue.

According to one embodiment, the first population of endonuclease-treated cells may also comprise one or more non-silent mutation(s) in said genomic region of interest.

According to one embodiment, the step b) of determining said genomic and reference signature is achieved by amplifying said genomic region of interest (i.e. with complementary primers to the said signatures and/or to a region encompassing said signature); wherein said primers are preferably suitable for real-time quantitative PCR (qPCR).

According to one embodiment, the step b) of determining said genomic and reference signature is achieved by real-time quantitative PCR.

According to one embodiment, the step b) of determining said genomic and reference signature is achieved by deep-sequencing.

The first and second population were treated by either one of the above-mentioned endonucleases, which includes endonucleases selected from: a Clustered Regularly Interspaced Short Palindromic Repeats (CRISPR)-CRISPR associated (Cas) (CRISPR-Cas) nuclease, a mega nuclease (MN), a zinc finger nuclease (ZFN), and a transcription activator-like effector nuclease (TALEN); and more particularly is a CRISPR-Cas nuclease.

Examples of CRISPR-Cas nucleases include Type II Cas9 and Type II-Cpf1 nucleases.

Accordingly, a preferred endonuclease is a Type II-Cas9 nuclease.

Methods for detecting a population of endonuclease-treated cells as described herein are particularly advantageous for the follow-up of one population of cells over the other in a sample (i.e. a composition or a biological tissue such as an isolated biological tissue), either in the presence or in the absence of a given stimulus or a particular experimental condition.

In a non-limitative manner, those methods can be implemented into screening methods for assessing:
the consequences of an oncogenic mutation in neuroblastoma-derived cells;
the resistance mechanisms associated with chemotherapy, such as in lung cancer; and/or
the study of cancer stem cells, in particular intratumor heterogeneity.

Each one of those embodiments can be combined.

Compositions & Kits

According to a third object, the invention relates to a composition comprising at least:
(i) a first population of endonuclease-treated cells, comprising one or more silent mutation(s) in a genomic region of interest, and optionally one or more non-silent mutation(s) in said genomic region of interest; and
(ii) a second population of endonuclease-treated cells, comprising one or more silent mutation(s) in said genomic region, but distinct from the silent mutations of the first population;

wherein the silent mutation(s) is/are introduced in said cells by HDR after treatment with a same endonuclease targeting the said genomic region of interest.

According to a preferred embodiment, said cells are eukaryotic cells.

Compositions which are considered by the invention include any medium that is suitable for cell growth, or formulation for addition, as desired, to conventional and available cell cultures.

According to one particular embodiment, a composition of the invention may be selected from a group comprising or consisting of: a pharmaceutical composition, a medicament, a growth medium or culture medium suitable for said cells.

According to one embodiment, a composition of the invention may be a composition that is suitable for parenteral or oral administration, and/or a sterile injection (i.e. intravenous or intraarterial or intra-tissue injection).

According to one embodiment, this composition is obtained by performing a method for labeling cells, most preferably eukaryotic cells, in a composition as described above.

According to one particular embodiment, said first and/or second population further comprise non-silent mutation(s) in said genomic region of interest.

In particular, the following alternatives are explicitly considered:

(i) said first population comprises non-silent mutations but not the second population; or (ii) said first and second populations both comprise non-silent mutation(s), said non-silent mutation(s) being the same or different, and preferably different.

Said first and second populations may be considered either in an isolated form or in the presence of other contaminants and/or distinct populations.

Accordingly, when said first and second populations are considered in an isolated form, they may be part of a substantially pure composition (i.e. a composition which does not comprise in a detectable manner any other population of cells).

Said first and second populations can also be considered in the form of a kit.

According to a fourth object, the invention relates to a kit for detecting a population of endonuclease-treated cells, most preferably eukaryotic cells, comprising at least:
  a first part comprising a first population of endonuclease-treated cells as defined above; and
  a second part comprising a second population of endonuclease-treated cells as defined above.

Accordingly, said first and second population of endonuclease-treated cells are preferably obtained after bringing into contact cells with (i) at least one endonuclease suitable for targeting a genomic region of interest in said cells, or vector suitable for expressing said endonuclease in said cell; and (ii) at least one nucleic acid suitable for introducing said silent mutation(s) in the genomic region of interest of said cells by HDR.

The first and second population were treated by either one of the above-mentioned endonucleases (such as DNA-guided and RNA-guided endonucleases), which includes endonucleases selected from: a Clustered Regularly Interspaced Short Palindromic Repeats (CRISPR)-CRISPR associated (Cas) (CRISPR-Cas) nuclease, an Argonaute (Ago) nuclease, a mega nuclease (MN), a zinc finger nuclease (ZFN), and a transcription activator-like effector nuclease (TALEN); and preferably is a CRISPR-Cas nuclease.

Accordingly, a preferred endonuclease is a Type II-Cas protein, such as Cas9 or Cpf1.

Accordingly, a preferred vector suitable for expressing said endonuclease is a CRISPR-Cas system, such as a CRISPR-Cas9 system or a CRISPR-Cpf1 system.

Alternatively, the endonuclease may be selected from Argonaute nuclease, which includes DNA-guided Argonaute nucleases and RNA-guided Argonaute nucleases.

According to a fifth object, the invention also relates to a kit for labeling Clustered Regularly Interspaced Short Palindromic Repeats (CRISPR)-CRISPR associated (Cas) (CRISPR-Cas) system-treated cells, most preferably eukaryotic cells, comprising:

(i) a first part comprising at least one CRISPR-Cas system comprising:

a) a first regulatory element operable in a cell operably linked to at least one nucleotide sequence encoding a CRISPR-Cas system guide nucleic acid that hybridizes with a target genomic region of interest of said cell, and b) a second regulatory element operable in said cell operably linked to a nucleotide sequence encoding a Cas endonuclease, preferably a. Type II-Cas9 protein, wherein components (a) and (b) are located on same or different vectors of the system;

(ii) a second part comprising at least one nucleic acid suitable for introducing silent mutation(s) in said genomic region of interest by HDR, and optionally one or more non-silent mutation(s) in said genomic region of interest.

The CRISPR-Cas system guide nucleic acid is preferably a CRISPR-Cas system guide RNA. Thus, the invention also relates to a kit for labeling Clustered Regularly Interspaced Short Palindromic Repeats (CRISPR)-CRISPR associated (Cas) (CRISPR-Cas) system-treated cells, most preferably eukaryotic cells, comprising:

(i) a first part comprising at least one CRISPR-Cas system comprising:

a) a first regulatory element operable in a cell operably linked to at least one nucleotide sequence encoding a CRISPR-Cas system guide RNA that hybridizes with a target genomic region of interest of said cell, and b) a second regulatory element operable in said cell operably linked to a nucleotide sequence encoding a Cas endonuclease, preferably a Type II-Cas9 protein, wherein components (a) and (b) are located on same or different vectors of the system;

(ii) a second part comprising at least one nucleic acid suitable for introducing silent mutation(s) in said genomic region of interest by HDR, and optionally one or more non-silent mutation(s) in said genomic region of interest.

According to one embodiment, components (a) and (b) of said CRISPR-Cas system are located on the same vector or nucleic acid.

According to one embodiment, said kit for labeling CRISPR-Cas system-treated cell(s) comprises:

(ii) at least one first nucleic acid suitable for introducing silent mutation(s) in said genomic region of interest of said cell(s) by HDR, and optionally one or more non-silent mutation(s); and (iii) at least one second nucleic acid suitable for introducing silent mutation(s) in the genomic region of interest of said cell(s), but distinct from the silent mutations of the first nucleic acid; wherein said nucleic acids are either within distinct parts or within the same part.

The kits which are described herein may further comprise one or more cell(s), in particular one or more eukaryotic cell(s), including cell(s) derived from a mammal or a plant.

According to some embodiments of the methods, compositions and kits described herein, the said silent mutation(s) are within:
- an open-reading frame (ORF) or exon of a gene coding for a protein of interest; or
- a non-coding region.

According to one preferred embodiment of the methods, compositions and kits described herein, the said silent mutation(s) are within an open reading frame (ORF) or exon of a gene coding for a protein of interest.

Each one of those embodiments can be combined.

EXAMPLES

A. Material & Methods

Cell Culture, Transfection, Lentiviral Production and Inhibitors 293T (human embryonic kidney), DLD-1, HCT-116 (colorectal carcinoma), MCF-7 (breast cancer) were obtained from ATCC, PC9 cells (NSCLC) were obtained from ECACC-Sigma-Aldrich, Kelly cells (neuroblastoma) were a kind gift from Dr. C. Einvik. All cells were grown in Dulbecco's modified Eagle's Medium (Life technologies) except Kelly and PC-9 cells, grown in Roswell Park Memorial Institute medium (Life technologies), both supplemented with 10% fetal bovine serum (FBS, Life Technologies) and 0.6% penicillin/streptomycin (Life technologies). Cells were transfected with a Nucleofector II device (Lonza) using the Amaxa Nucleofector kit (Lonza) and electroporation program recommended by the manufacturer. 293T cells were transfected using polyethylenimine (Polysciences). The efficiency of each transfection was assessed in parallel using a GFP-containing plasmid.

The Wnt-responsive construct was generated by cloning the Wnt-responsive promoter from a previously described reporter (Grumolato et al., 2013), followed by a destabilized GFP (Matsuda and Cepko, 2007) into the VIRSP lentiviral vector, containing the puromycin resistance gene. For lentivirus production, 293T cells were cotransfected with the Wnt-responsive lentiviral vector, pCMV Δ8.91 and pMD VSV-G plasmids. Two days after transfection, the conditioned medium was collected, purified by centrifugation, supplemented with 8 μg/mL polybrene, and added for overnight incubation to freshly plated DLD1 cells. Two days after infection, the cells were selected in 2 mg/mL puromycin.

Nutlin-3 was purchased from SelleckChem and doxorubicin was purchased from Abcam. The ATM inhibitor, the ALK inhibitor and the EGFR inhibitors were purchased from Santa-Cruz Biotechnology.

CRISPR Barcoding sgRNA target sequences (See Sequence Listing—SEQ ID No 1-14) were designed using the CRISPR Design tool hosted by the Massachusetts Institute of Technology (see the website located at crispr.mit,edu) to minimize potential off-target effects. Oligos encoding the targeting sequence were then annealed and ligated into the pSpCas9(BB)-2A-Puro (Ran et al., 2013) vector digested with Bbsl (New England Biolabs). The sequence of the ssODNs (Integrated DNA Technologies) used for CRISPR/Cas9-mediated HDR, containing one missense/nonsense mutation coupled with different silent mutations, are provided in the sequence listing (SEQ ID No 15-29). The set of silent mutations is designed to enable PCR specificity and to avoid recognition by the corresponding sgRNA used to cleave the endogenous sequence. For each targeted locus, cells were co-transfected with 2 μg of the CRISPR/Cas9 plasmid and 24 of either the control or the sense/nonsense ssODN (50 μM). Immediately after transfection, the cells were pooled in the same flask. For AAVS1 barcoding, BT474 cells were subjected to two rounds of transfection at two weeks interval using CRISPR/Cas9 plasmids encoding two distinct sgRNAs, together with a ssODN containing nine degenerate nucleotides and a SalI restriction site (See Sequence Listing—respectively SEQ ID No 13-14 and 29).

qPCR, PCR and Surveyor Assay and RFLP Assay gDNA was extracted using the NucleoSpin Tissue kit (Macherey-Nagel). Total RNA was isolated using the Tri-Reagent (Sigma-Aldrich) and the RNeasy kit (Qiagen), DNase digested and reverse-transcribed using the Improm-II Reverse Transcription System (Promega). The sequence of the different PCR primers, designed using Primer-BLAST (NCBI), is provided in the sequence listing (SEQ ID N°30-57). To avoid potential amplification from ssODN molecules not integrated in the correct genomic locus, one of the two primers was designed to target the endogenous genomic sequence flanking the region sharing homology with the ssODNs. Primer specificity for each particular barcode was assessed. qPCR was performed from 100 ng of gDNA using SYBR Green (Life Technologies) on a 7900 HT Fast-Real-Time, a Q-PCR ABI PRISM 7500 or a QuantStudio Flex PCR System (Life Technologies). qPCR analysis was performed using the standard curve or the Pfaffl methods (Pfaffl, 2001).

The sequence of the primers used to amplify a ~800 bp region of the APC and AAVS1 genes encompassing the CRISPR/Cas9 targeted sites is provided in the sequence listing (SEQ ID N°58-61). PCR was performed using Herculase II Fusion DNA Polymerase (Agilent Technologies) and the amplicon was purified using PCR clean-up kit (Macherey-Nagel) and eluted with 30 μL of TE buffer. Surveyor assay was performed as described (Ran et al., 2013). Briefly, 15 μL of purified-PCR products were then mixed with Taq polymerase PCR buffer and subjected to a re-annealing process to enable DNA hetereoduplex formation. After re-annealing, products were treated with SURVEYOR nuclease and SURVEYOR enhancer S (Transgenomic). The remaining 15 μL of the purified amplicon was used as a control. For RFLP assay, the AAVS1 amplicons were digested in the presence or in the absence of SalI (Promega). For both surveyor and RFLP assays, the reaction products were analyzed on a 10% Acrylamide-TBE gel stained with SYBR-Gold (Life Technologies) and imaged with a Chemidoc gel imaging system (Bio-Rad).

Barcoding Detection Through Multiplex TaqMan PCR

The T790T and T790M barcodes in gDNA samples from PC9 cells were detected by multiplex TaqMan PCR using a couple of unmodified forward and reverse primers, together with a TaqMan QSY probe targeting the T790T barcode (FAM dye, Life Technologies) and a TaqMan QSY probe targeting the T790M barcode (ABY dye, Life Technologies). To limit amplification of the endogenous sequence, a specific blocking oligonucleotide, containing phosphorothioate bonds and a ddC in 3' (Eurofins Genomics), was added to the reaction. The reactions were performed in the presence of 1× TaqMan Multiplex Master Mix (Life technologies) on a QuantStudio Flex PCR System (Life Technologies). The sequence of the primers and probes is provided in the sequence listing.

RNA Extraction and Reverse Transcription

Total RNA was isolated using the Tri-Reagent (Sigma-Aldrich) and the RNeasy kit (Qiagen), DNase digested and reverse-transcribed using the Improm-II Reverse Transcription System (Promega).

Cell Sorting by FACS

DLD1 cells transduced with the Wnt-responsive reporter were sorted based on the level of GFP expression. Briefly, harvested cells were resuspended in sterile FACS-sorting buffer (D-PBS medium, 2 mM EDTA, 0.5% BSA), filtered on 30 µm cell-strainer filters (BD Biosciences) to remove cell aggregates and isolated by FACS using a FACSAria-III Cytometer (BD Biosciences). DLD1 cells containing the Wnt reporter were first sorted to deplete the fraction of cells expressing low levels of GFP. The resulting DLD1 cell population was transfected for APC CRISPR-barcoding, and five days later $GFP^{hi}$ (defined as the 10% of the cells displaying the highest fluorescence) and $GFP^{lo}$ cells (defined as the 10% of the cells displaying the lowest fluorescence) were isolated by FACS. gDNA was extracted from sorted and un-sorted cells for qPCR analysis. Cells were maintained at 4° C. during the entire sorting procedure. Reanalysis of sorted fractions consistently showed that more than 95% of the sorted cells were viable and corresponded to the defined $GFP^{hi}$ or $GFP^{lo}$ gates. Analysis and graphical representation of the data were performed using FlowJo software (Tree stars).

APC Deep Sequencing

PCR was performed from DLD1 cell gDNA samples using Herculase II Fusion DNA Polymerase and two couples of primers (Sequence Listing—SEQ ID N°58-72), designed to amplify two overlapping regions of the APC gene spanning 245 and 220 bp, respectively, both including the CRISPR/Cas9 targeted sequence. The samples were prepared from 1 µg of purified amplicons using SPRIworks System I automaton (Beckman). Each couple of amplicons was indexed with the same adapter sequence (Craig et al., 2008), and the enriched libraries were sequenced on a Genome Analyzer IIx (Illumina) with 76 bp paired-end reads. Image analysis and base calling were performed by Real-Time Analysis (RTA 1.9) and CASAVA software (v1.8.2, Illumina). The mean read count passing filters for each sample was at least 160,000, and 94% of the sequenced bases have a QScore above 30. Motifs of interest were counted in the FastQ files.

Invasion Assay

PC9 cells containing the EGFR-T790M and -T790T barcodes pre-treated or not with gefitinib (0.5 µM) for 48 hr were seeded in matrigel 6-well invasion chambers (8 µM pores; BD Biosciences) at a density of $1.5 \times 10^6$ cells per chamber, in the presence or the absence of gefitinib (0.5 µM) and incubated for 24 hr. As a control, a fraction of the cells was seeded in parallel in regular wells. The cells inside and outside the chambers were then trypsinized and gDNA was extracted for qPCR.

Mouse Xenografts

PC9 cells containing the EGFR-T790, KRAS-G12 and EML4-ALK barcodes were resuspended in PBS and subcutaneously inoculated in the left and right flank ($2 \times 10^6$ cells per site) of male SCID mice (NCI). The size of the tumors was measured by caliper every 3-4 days. Sixteen days after injection; when the tumors were palpable, half of the mice were treated 5 days a week with gefitinib (25 mg/kg/day) by gavage. When the size of at least one of the tumors reached the arbitrary volume of 550 mm³, the mice were sacrificed and gDNA was extracted from the tumors for qPCR analysis. BT474 cells ($5*10^6$ cells per site) were mixed with matrigel and inoculated bilaterally in the mammary fat pad of female SCID mice previously implanted with 17β-estradiol pellets (Innovative Research of America). Mice were sacrificed 3, 4 and 5 weeks after injection and gDNA was extracted from the tumors for deep sequencing analysis. At each time point, gDNA was extracted from the same batch of BT474 cells kept in culture. All animal experiments were approved and performed according to the relevant regulatory standards set by Mount Sinai's Animal Care and Use Committee.

Immunoblot

Cells were washed once with phosphate-buffered saline (PBS) and lysed on ice in lysis buffer containing 50 mM Hepes pH 7.6, 150 mM NaCl, 5 mM EDTA, 1% Nonidet P-40, 20 mM NAF, 2 mM sodium orthovanadate, supplemented with protease inhibitor mini tablets (Thermo Scientific). Lysates were cleared by centrifugation at 14,000 g during 15 min at 4° C. and protein concentrations were determined by using the Bio-Rad protein assay (Bio-Rad). Sodium dodecyl sulfate (SDS) loading buffer was added to equal amounts of lysate, followed by SDS-polyacrylamide gel electrophoresis (SDS-PAGE) and transfer to polyvinylidene fluoride (PVDF) membrane (Thermo Scientific). The membranes were probed using Mouse anti-TP53 (Cell Signaling) and mouse anti-β-catenin (BD Biosciences) antibodies and analyzed by chemiluminescence using ECL Western Blotting Substrate (Thermo Scientific).

B. Results

1. Restoration of the Tumor Suppressor APC in Colorectal Cancer Cells Through CRISPR-Barcoding We used CRISPR-barcoding to investigate the effects of restoring APC function in DLD-1 colorectal cancer cells, which harbor a homozygous frameshift mutation in position c.4248 (Data not shown). To this end, we designed a specific sgRNA and a ssODN(APC-WT), containing the repaired wild-type APC coding sequence, as well as a few additional silent mutations to serve as a genetic barcode.

Figure 1A:
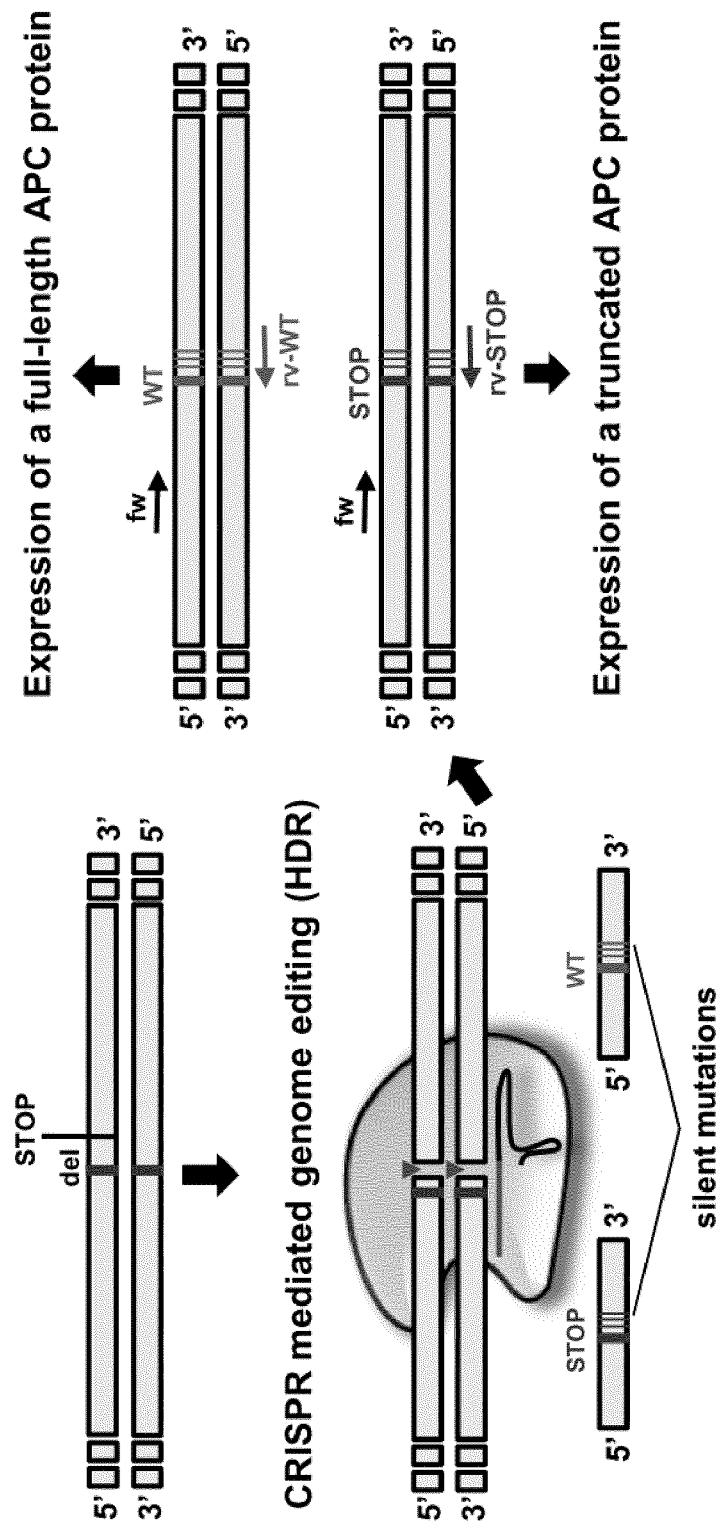
FIG. 1: Restoration of Functional APC in Colorectal Cancer Cell Through CRISPR-Barcoding A. Schematic of the incorporation of APC-WT and APC-STOP (control) barcodes to restore the function of the APC gene in colorectal cancer cells. The position of forward and reverse primers for PCR is indicated with arrows.

As a control for potential CRISPR/Cas9 off-target cleavage, we generated a ssODN(APC-STOP), containing a distinct barcode unable to restore the expression of a full-length APC protein (FIG. 1A). To prevent the potential incorporation of the two donor DNA sequences into different alleles of the same cell, DLD-1 cells were co-transfected separately with the CRISPR/Cas9 plasmid, encoding Cas9 and the sgRNA, and either ssODN(APC-WT) or ssODN(APC-STOP). Immediately after transfection, the cells were pooled to form a mixed population of unmodified, APC-WT and APC-STOP cells. PCR primers were designed that specifically recognize the APC-WT or the APC-STOP barcodes (data not shown).

Figure 1B:
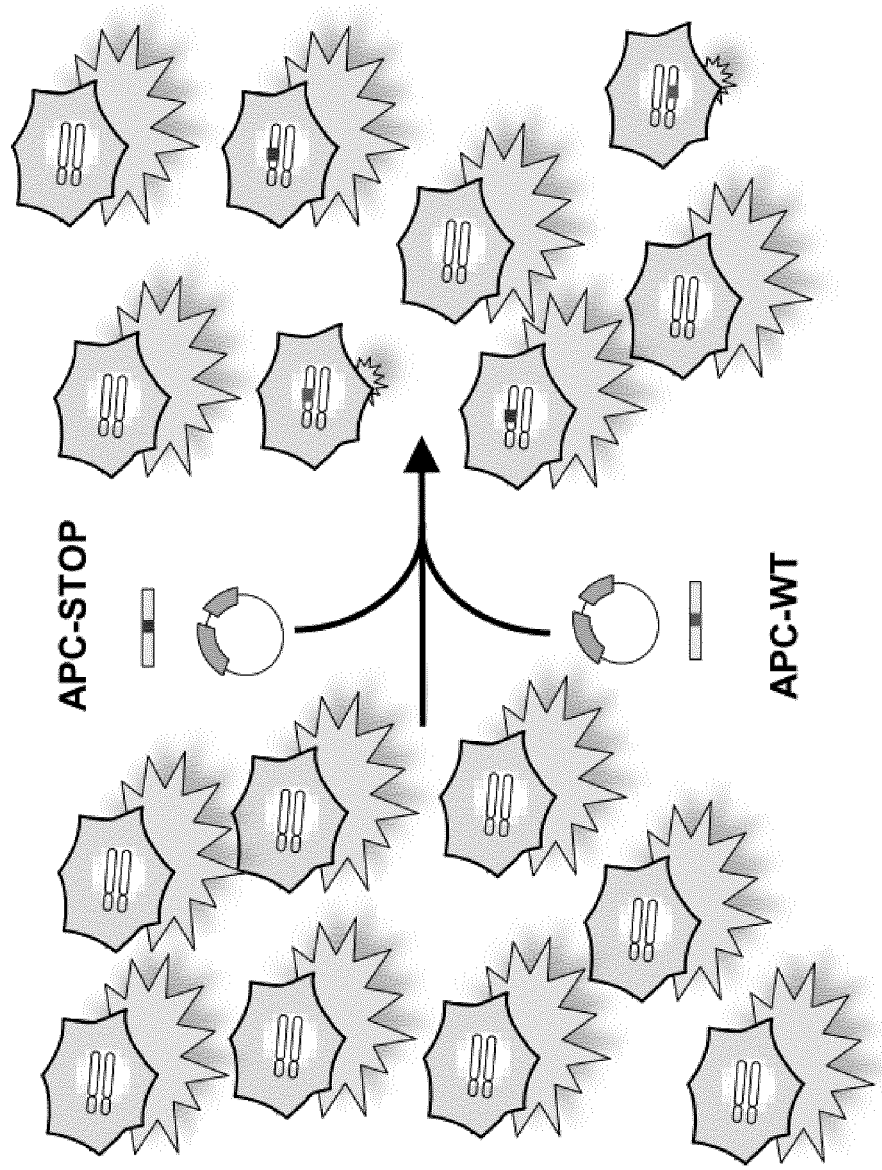
Figure 1C:
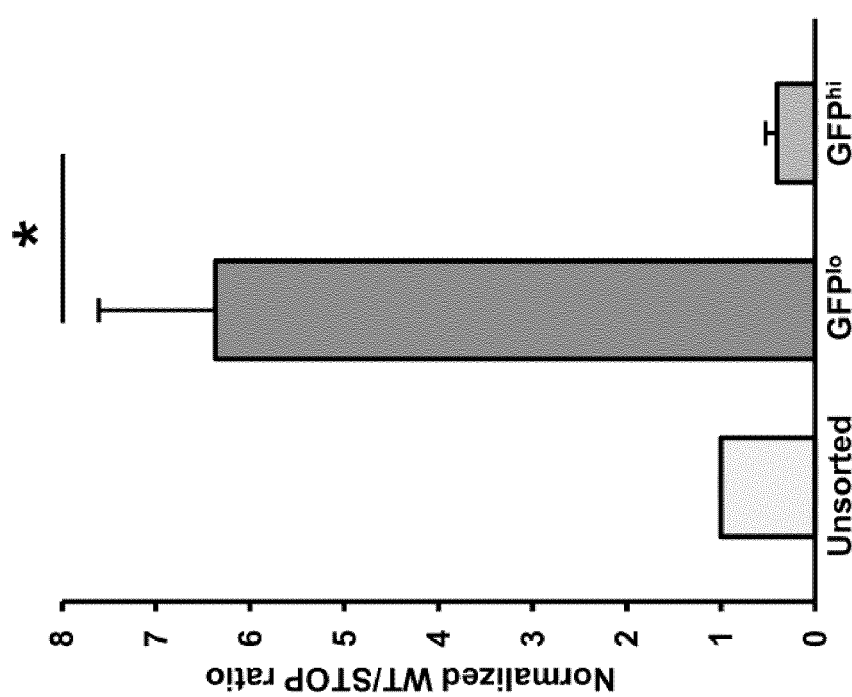
Figure 1D:
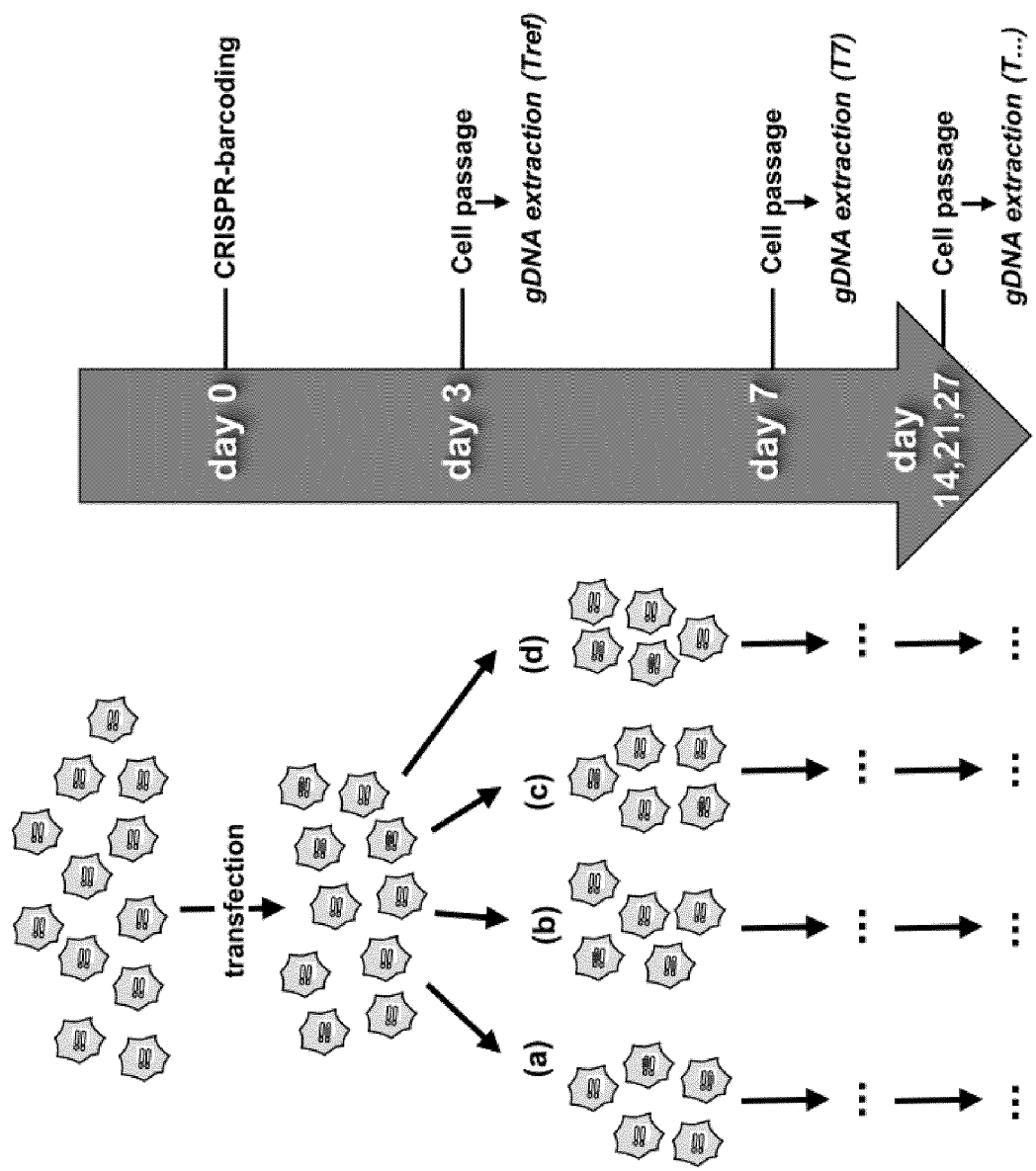

Restoration of a full-length APC protein in APC-mutant colorectal cancer cells is expected to down-regulate the Wnt signaling pathway. As a means to measure Wnt activation in these cells, we used a lentiviral reporter containing a destabilized form of GFP, driven by a minimal promoter containing 14 Wnt-responsive elements. DLD-1 cells stably containing the Wnt reporter were transfected for APC CRISPR-barcoding as illustrated in FIG. 1B. Five days after transfection, the cells were FACS sorted to isolate the 10% of cells displaying the highest ($GFP^{hi}$) or lowest ($GFP^{lo}$) GFP levels (FIG. 1C). As shown in FIG. 1D, qPCR analysis from genomic DNA (gDNA) revealed a strong enrichment of the APC-WT compared to the APC-STOP barcode in the $GFP^{lo}$ cells. Conversely, APC-WT was depleted in $GFP^{hi}$ cells, consistent with Wnt signaling inhibition in cells containing a repaired APC gene.

Figure 1E:
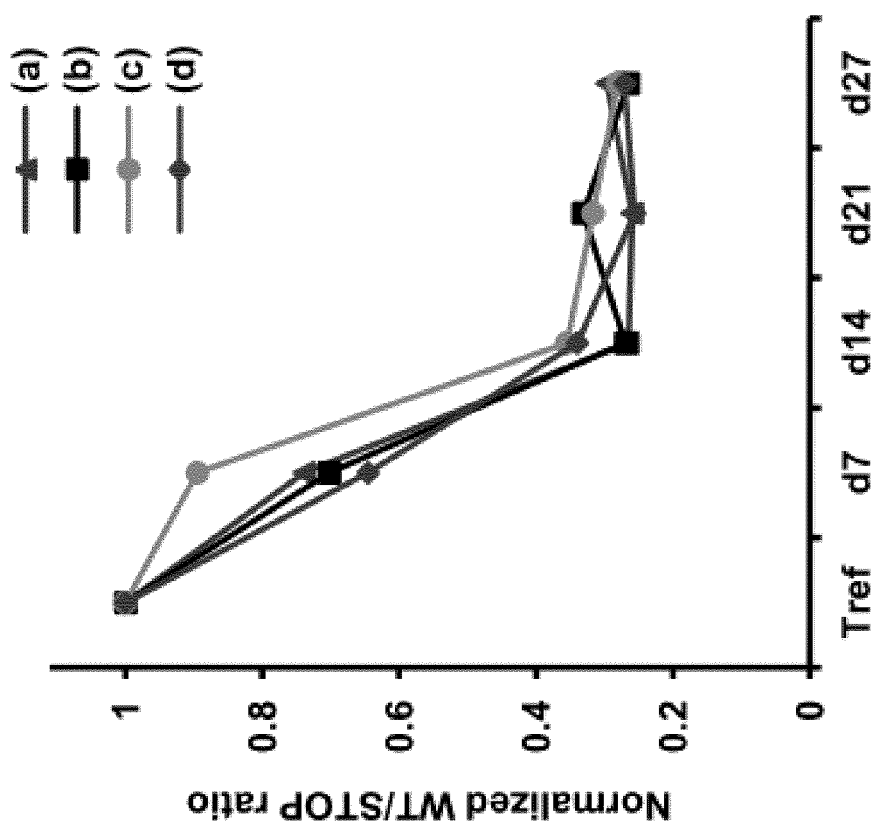
Figure 1F:
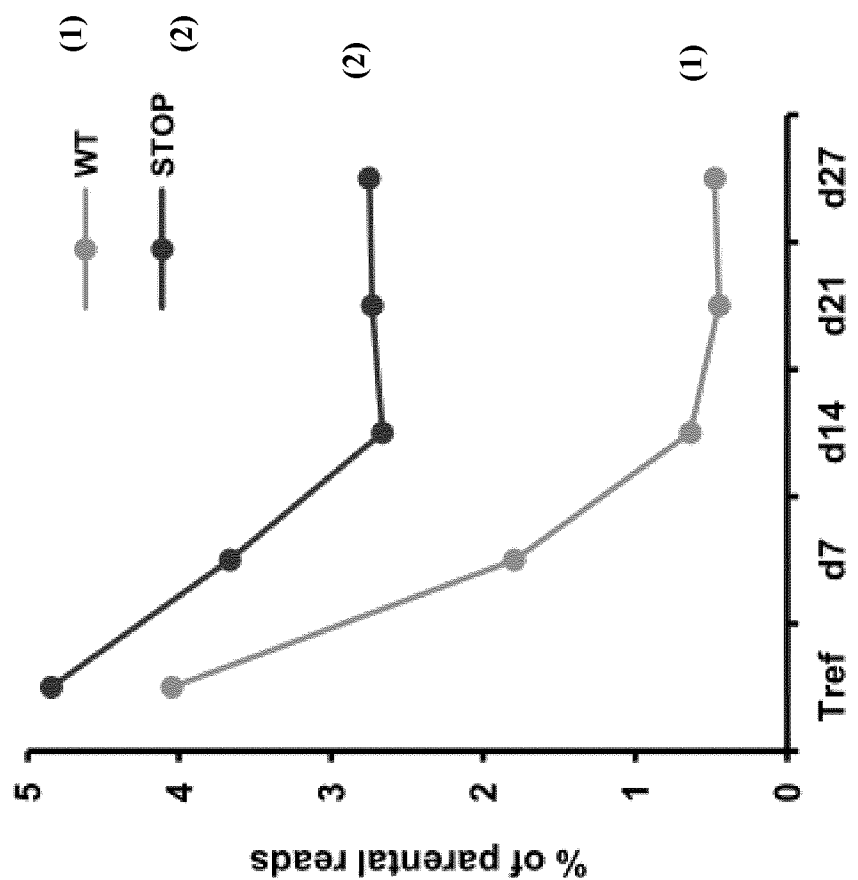

It has been shown that Wnt inhibition through the expression of a dominant-negative construct can induce colorectal cancer cell growth arrest (van de Wetering et al., 2002). To assess the effects of APC gene repair on DLD-1 cell growth, parental cells were co-transfected with the CRISPR/Cas9 plasmid and the APC-WT or APC-STOP ssODNs and immediately mixed. Three days after transfection, corresponding to the time of reference (Tref), the cells were trypsinized, replated into four different flasks and propagated for about four weeks. At each cell passage, gDNA was extracted for qPCR analysis (FIG. 1E). As shown in FIG. 1F, the fraction of DLD-1 cells containing the APC-WT compared to the APC-STOP barcode strongly decreased over time, reaching a plateau at two weeks after transfection (FIG. 1F). Similar results were obtained using a different sgRNA (Data not shown), consistent with the addiction of colorectal cancer cells to activated Wnt signaling. Of note, when the APC-WT and APC-STOP levels were normalized to, the total amount of DNA, we found that at early time points the proportion of both barcodes decreased, albeit to a different extent (Data not shown). This effect could conceivably derive from an APC-independent delay in cell cycle progression provoked either by the sgRNA-mediated cleavage of off-target sequences, or by the response to DNA damage induced by CRISPR/Cas9, strongly emphasizing the need of an internal control for gene editing specificity.

As a support to the qPCR data, we deep sequenced the region of the APC gene targeted by CRISPR/Cas9 from the gDNA samples used in FIG. 1F. FIG. 1G shows that the proportion of APC-WT reads dramatically decreases compared to the reads containing the APC-STOP barcode, consistent with a negative pressure against the cells in which full-length APC was restored. Intriguingly, we found that the proportion of APC-WT reads containing frameshift mutations increased six-fold at day 27 compared to the Tref (Data not shown), consistent with a positive selection of "false" APC-WT barcodes, unable to restore full-length APC protein. The enrichment of these sequences, probably originated during the homology-directed repair (HDR) process or the synthesis of the ssODN, could explain the persistence of a small, but stable population of cells retaining the APC-WT barcode (FIGS. 1F-G).

This experiment provides evidence for the need of internal controls for gene editing specificity, and also the practical application of endonuclease barcoding, in particular CRISPR-Barcoding, for studying the impact of genes on cell growth, on cell differentiation, on cell motility and invasion, and on signaling pathway regulation.

2. TP53 Inactivation Using CRISPR-Barcoding

In diploid cells, CRISPR/Cas9 editing can affect one or both alleles, resulting in heterozygous or homozygous modifications (Ran et al., 2013). The distribution of edited versus unedited alleles can be more complex in cancer cells, which are often aneuploid. In our DLD-1 colon cancer model, the genetic modification generated by CRISPR/Cas9 exerted a dominant effect, since the repair of just one allele of APC was conceivably sufficient to restore the expression of a full-length APC protein and, consequently, to inhibit Wnt signaling and cell growth. We sought whether CRISPR-barcoding could be applied more generally to investigate the function of genes for which both alleles can contribute to the cell phenotype.

It has been reported that the rate of NHEJ repair following CRISPR/Cas9-induced DNA cleavage is considerably higher compared to HDR (Hsu et al., 2014). Consistent with these observations, deep sequencing and surveyor assay revealed that in DLD-1 cells the fraction of APC alleles containing indels or any barcode were approximately 30-50% and 5-6%, respectively (FIG. 1F & Data not shown). We speculated that if in a particular cell the CRISPR/Cas9 activity is sufficient to enable the insertion of a barcode on one allele, in many cases it would also provoke the inactivation of the second allele by NHEJ, thus resulting in a dominant effect of the barcode. To test this hypothesis, we used CRISPR-barcoding to inactivate the TP53 tumor suppressor gene. In response to a variety of cellular stressors, including DNA damage, nutrient deprivation and onco-gene activation, TP53 is stabilized at the protein level and acts as a transcription factor to regulate the expression of different target genes, resulting in cell-cycle arrest, senescence, autophagy or apoptosis. TP53 stabilization can also be artificially induced using small molecule inhibitors, such as Nutlin 3, which blocks the interaction between TP53 and the E3 ubiquitin ligase MDM2. To inactivate the gene encoding this tumor suppressor, we designed a ssODN (TP53-STOP) to introduce a STOP codon to replace Phe109, located at the beginning of the DNA-binding domain and downstream to the transactivation and proline-rich domains (Data not shown).

In parallel, a control ssODN(p53-WT), containing only silent mutations, was also generated. As described above for APC and DLD-1 cells, we performed TP53 CRISPR-barcoding in two widely used cancer lines presenting a wild-type TP53 gene, i.e. breast MCF7 and colon HCT-116 cancer cells, both wild-type for the TP53 gene (see the website located at p53.iarcfr/CellLines.aspx). Treatment with Nutlin 3 (Data not shown) significantly increased the fraction of MCF7 and HCT-116 cells containing the TP53-STOP barcode, consistent with loss of TP53 activity in these cells, thus supporting the application of CRISPR-barcoding in models where two alleles contribute to the function of a particular gene.

Despite exerting similar or stronger effects than Nutlin 3 on TP53 induction and cell growth inhibition (Data not shown), the genotoxic agent doxorubicin did not affect the relative proportion of the two barcodes, supporting the notion that TP53 is not strictly required for the activation of DNA damage checkpoints (Data not shown).

This experiment provides evidence that endonuclease barcoding, in particular CRISPR-Barcoding, can be applied to genes for which both alleles can contribute to a cell phenotype; and optionally to inactivating said genes.

3. Repair of ALK-F1174L Oncogenic Mutation in Neuroblastoma Cells

The general strategy to investigate the oncogenic properties of a putative gain-of-function mutation involves the exogenous and potentially non-physiological expression of the mutant gene or the time-consuming generation of knock-in models. To demonstrate the suitability of CRISPR-barcoding as an alternative approach, we chose the anaplastic lymphoma kinase (ALK), a receptor tyrosine kinase (RTK) mutated in 6-10% of neuroblastomas. As a model, we used the neuroblastoma cell line Kelly, containing a heterozygous F1174L mutation in the catalytic domain of this receptor (Data not shown).

Using the same approach described for APC and p53, we applied the CRISPR/Cas9 technology to introduce three distinct barcodes in the genome of Kelly cells:

(i) ALK-F1174F, to repair the oncogenic mutation;

(ii) ALK-F1174L, as a control for the mutated receptor;

(iii) ALK-STOP, to generate a truncated protein lacking most of the intracellular domain, including the catalytic domain.

Because the parental cells contain a wild-type and a F1174L allele, the incorporation of each barcode can result in four possible combinations: for three of them, including the most likely barcode/indel, the phenotypically dominant ALK sequence expressed in the cell is expected to be the one encoded by the barcode (See FIG. 3). Following ALK CRISPR-barcoding, the fraction of F1174L cells remained stable, while the F1174F and STOP barcodes similarly decreased over time. The same results were obtained using a distinct sgRNA (Data not shown), indicating that the F1174L mutation is strictly required for the effect of ALK on the growth of these cells.

The silent mutations that compose a CRISPR-barcode may conceivably have an impact on the stability of the corresponding transcript. While this would be irrelevant for a STOP barcode, differences in the expression levels of a particular allele caused by such mutations could translate into false-positive or false-negative effects on the phenotype of the cells.

Yet, the relative fraction of the different barcodes in the gDNA compared to the cDNA extracted in parallel from the same cells did not reveal substantial effects on gene expression of a particular set of silent mutations (Data Not Shown).

As an additional control, we swapped the silent mutations on the F1174F and F1174L barcodes. Consistent with the previous data, the "swapped" barcodes confirmed that the cells containing the wild-type or the STOP codon are subjected to a similar growth disadvantage (Data not shown), thus excluding a potential bias due to an unwarranted effect of the silent mutations on mRNA stability.

To further demonstrate the specificity of our approach, we tested whether inhibiting ALK kinase activity could alter the proportion of the different barcodes. We investigated the effects of inhibiting the kinase activity of this receptor, by showing that the fractions of ALK-F1174F and ALK-STOP cells decreased significantly less in the presence of a small molecule, indicating that the selective pressure that favors the expression of a mutant receptor is abolished upon inhibition of ALK catalytic activity.

This experiment provides evidence that endonuclease barcoding, in particular CRISPR-Barcoding, can be applied by introducing multiple barcodes in the same genomic locus of cancer cell lines.

It also provides evidence that the swapping of silent mutations (between barcodes) can be used as an additional control against unwarranted effects due to potential variations in the expression levels of the gene of interest that might be provoked by said silent mutations.

4. Chemotherapy Resistance in Lung Cancer Cells

A major limitation of cancer targeted therapies is the almost inevitable development of an acquired resistance. As a typical example, gefitinib and erlotinib are small molecule inhibitors of the epidermal growth factor receptor (EGFR) that are used in the clinic for the treatment of advanced non-small-cell lung cancers (NSCLC) harboring EGFR activating mutations. After an initial response to these inhibitors, the tumors invariably relapse, as a result of the emergence of a subpopulation of resistant cancer cells. The most common molecular mechanism responsible for the acquired resistance to EGFR inhibitors in NSCLC is the appearance of the T790M secondary mutation in the catalytic domain of this receptor.

Using the same approach described above, we introduced a EGFR-T790M and a EGFR-T790T control barcode in PC9 cells, a gefitinib/erlotinib sensitive cell line derived from NSCLC harboring a small in frame deletion (p.E746_A750del) on EGFR exon 19. Because of the EGFR-T790T internal control, the CRISPR-barcoding approach allows specificity over a wide range of inhibitor concentrations. Indeed, an enrichment of EGFR-T790M containing cells was readily detectable after four days of gefitinib treatment at a concentration of 10 nM, while a stronger effect was observed at higher doses (Data not shown).

Thus, the CRISPR-barcoding approach allows specificity over a wide range of inhibitor concentrations.

Point mutations of the KRAS oncogene are among the most frequent genetic aberrations in NSCLC. Extremely rare in tumors containing mutant EGFR, KRAS mutations represent a typical mechanism of primary resistance to EGFR inhibitors. We used CRISPR-barcoding to insert the G12D KRAS mutation in PC9 cells, which were then treated in the presence or the absence of gefitinib. The EGFR inhibitor induced a significant enrichment of KRAS-G12D cells, indicating that gefitinib resistance in PC9 cells can also be conferred by mutant KRAS.

We next investigated the effects of a third generation EGFR irreversible inhibitor designed to selectively target the T790M mutant receptor. We show that the expansion of cells containing the EGFR-T790M barcode in the presence of gefitinib was abolished by co-treatment with this inhibitor, consistent with a different target specificity of these two classes of EGFR inhibitors. Conversely, the relative fraction of KRAS-G12D cells was significantly increased in the presence of the inhibitor, reflecting a downstream activation of EGFR signaling in these cells.

EGFR can stimulate cell migration and invasion through direct activation of downstream effectors, including Src and STATS, or by promoting epithelial to mesenchymal transition. The overwhelming effects on cell proliferation and survival have hampered investigations of the role of EGFR signaling in the invasiveness of NSCLC cells. As a means to overcome the potential bias due to cell growth inhibition, we used CRISPR-barcoding to assess the effects of gefitinib on PC9 cell invasion. EGFR-barcoded PC9 cells were pretreated for two days with gefitinib, then transferred to Boyden chambers containing matrigel. Twenty-four hours later, the cells inside and outside the Boyden chamber i.e. on sides of the polycarbonate membrane, i.e., were collected and gDNA was extracted (see FIG. 4).

We show that the EGFR-T790M barcode was dramatically enriched in the cells that migrated through the matrigel-coated membrane, as compared to those that remained inside the chamber, indicating that EGFR signaling strongly contributes to the invasive properties of these cancer cells. As a control, the proportion of the two EGFR barcodes in each compartment remained constant in the absence of gefitinib treatment (Data not shown). By measuring the relative proportion of the barcoded cells on both sides of the chamber, our approach allows a specific and quantitative analysis of cell invasion, regardless of any potential effect on cell proliferation and survival.

This experiment provides evidence of the practical application of endonuclease barcoding, in particular CRISPR-Barcoding, to assess drug specificity, for drug screening, for studying cell invasion and on distinct targets.

5. Multiplexed CRISPR-Barcoding for In Vitro and In Vivo Studies

Identification of chromosomal rearrangements involving the ALK gene in a significant fraction of metastatic NSCLCs has led to the approval of specific ALK inhibitors for the treatment of this type of cancer. The most frequent of such rearrangements corresponds to an inversion on chromosome 2, resulting in the expression of a constitutively active fusion protein, composed of the echinoderm microtubule-associated protein-like 4 (EML4) and ALK. Recently, the EML4-ALK inversion has been reproduced artificially in both cultured cells and mouse kings using the CRISPR/Cas9 technology. To extend the potential applications of CRISPR-barcoding to this type of genetic aberrations, we simultaneously induced the cleavage of the EML4 and ALK genes in PC9 cells through co-expression of Cas9 and two distinct sgRNAs as previously described.

To increase the efficiency of the chromosomal inversion, the cells were co-transfected with a ssODN encompassing the rearranged EML4-ALK sequence (Data not shown). qPCR primers were designed to specifically recognize the inverted locus, here acting as a sort of genetic barcode for cells expression the oncogenic EML4-ALK protein (Data not shown). Gefitinib treatment induced an enrichment of EML4-ALK containing PC9 cells, indicating that this chromosomal rearrangement could represent a new mechanism for acquired resistance to EGFR inhibitors.

As a proof-of-concept, we co-introduced in the same PC9 cell culture the three modifications described above, capable of conferring resistance to EGFR inhibition, i.e. EGFR-T790M, KRAS-G12D and EML4-ALK. Consistent with the data obtained with individual mutations, gefitinib treatment of multiplex CRISPR-barcoded PC9 cells induced a specific enrichment of the EGFR-T790M, KRAS-G12D and EML4-ALK sequences (FIG. 2). We show that the resistance to gefitinib induced by EGFR-T790M and EML4-ALK was specifically blocked by co-treatment with an EGFR irreversible inhibitor or a ALK inhibitor, while these compounds had no effect on the fraction of cells containing the KRAS-G12D barcode.

Based on a mix of genetically labeled cell subpopulations, CRISPR-barcoding can be adapted to multiplexing.

This experiment provides evidence that endonuclease barcoding, in particular CRISPR-Barcoding, can be easily implemented in a multiplex setting, in which cell subpopulations containing barcodes for the same or different genomic locations can coexist in the same mass population. Such strategy is particularly suitable for, but not limited to, drug screening.

Because high-throughput screens need increased levels of automatization, we devised a different qPCR readout strategy for barcode detection. PCR is performed in the presence of distinct TaqMan probes that are specific to each barcode and contain distinct fluorescent dyes. To hinder the amplification of the more abundant native sequence, which could lead to premature exhaustion of primers and other PCR components, the reaction also included a blocking oligonucleotide resistant to the 5'-exonuclease activity of the DNA polymerase and unable to prime extension, which was specifically designed to hybridize to the parental, unmodified sequence. For each gDNA sample, the normalized fluorescence for each dye allows to quantify in one single PCR reaction the fraction of the mutant versus the control barcode. We used this approach to investigate the effects of various compounds on gefitinib resistance in EGFR-T790 barcoded PC9 cells.

This experiment provides evidence that multiplex TaqMan PCR can be conveniently used for detection of endonuclease barcodes, in particular CRISPR-barcodes, including high-throughput applications (i.e. high-throughput screening).

To illustrate the potential applications of our strategy to in vivo studies, multiplex CRISPR-barcoded PC9 cells were subcutaneously and bilaterally injected in immunocompromised mice (Data not shown). Sixteen days after injection, when tumors were palpable, half of the mice were treated with gefitinib (25 mg/kg/day). As expected, the growth of the tumors was initially arrested upon gefitinib treatment, but it eventually resumed after a few weeks (Data not shown), mimicking the pattern typically observed in the clinic for NSCLC patients treated with this inhibitor. When at least one of the two tumors exceeded the arbitrary volume of 550 $mm^3$, the mice were sacrificed and gDNA was derived from the tumors. The frequency of the three different mutations in the tumor samples was measured by qPCR and normalized to the levels observed in the same batch of cells prior to injection in the mice. It was shown that the proportion of all three mutations was strongly increased in the tumors from gefitinib treated mice, albeit the relative enrichment was different in each tumor.

6. Probing Intratumor Heterogeneity Using Degenerate CRISPR-Barcodes

The fact that individual tumors contain a certain degree of genetic and/or phenotypic heterogeneity, which can vary substantially according to the tumor type, can have fundamental repercussions in cancer treatment. Different strategies have been used to isolate and functionally characterize particular cell subpopulations within a tumor, including FACS sorting, mouse genetic lineage-tracing and viral labeling. We reasoned that CRISPR-barcoding could be easily adapted to tag individual cancer cells within a mass population by using a ssODN containing different degenerate nucleotides. As a proof-of-concept, we targeted the AAVS1 locus on chromosome 19, a genomic "safe harbor" widely used for transgene insertion, in BT474 breast cancer cells, a cell line displaying high efficiency of CRISPR/Cas9 DNA editing (Data not shown). The cells were sequentially transfected for CRISPR-barcoding with two distinct sgRNAs (SEQ ID N°13-14), and a degenerate set of ssODNs containing a SalI restriction site (SEQ ID N°29) was used to allow Restriction Fragment Length Polymorphism (RFLP)-PCR quantification of the fraction of cells containing a genetic label (FIG. 6). After barcoding, part of the cells was bilaterally injected in the fat pad of immunocompromised mice, while the rest was maintained in culture. At different time-points, the mice were sacrificed and gDNA was derived from both the tumors and the cells in culture for deep sequencing analysis of barcode complexity in the different samples (Data not shown).

These experiments provide evidence that endonuclease barcoding, in particular CRISPR-Barcoding, can be applied to in vivo studies, including, but not limited to labeling of individual cancer cells within a mass population using degenerate barcodes.

BIBLIOGRAPHIC REFERENCES

Doudna, J. A., and Charpentier, E. (2014). Genome editing. The new frontier of genome engineering with CRISPR-Cas9. Science 346, 1258096.

Hsu, P. D., Lander, E. S., and Zhang, F. (2014). Development and applications of CRISPR-Cas9 for genome engineering. Cell 157, 1262-1278.

Barrangou, R., and Marraffini, L. A. (2014). CRISPR-Cas systems: Prokaryotes upgrade to adaptive immunity. Molecular cell 54, 234-244.

Ran, F. A., Hsu, P. D., Wright, J., Agarwala, V., Scott, D. A., and Zhang, F. (2013). Genome engineering using the CRISPR-Cas9 system. Nature protocols 8, 2281-2308

Grumolato, L., Liu, G., Haremaki, T., Mungamuri, S. K., Mong, P., Akiri, G., Lopez-Bergami, P., Arita, A., Anouar, Y., Mlodzik, M., et al. (2013). beta-Catenin-independent activation of TCF1/LEF1 in human hematopoietic tumor cells through interaction with ATF2 transcription factors. PLoS genetics 9, e1003603.

Matsuda, T., and Cepko, C. L. (2007). Controlled expression of transgenes introduced by in vivo electroporation.

Proceedings of the National Academy of Sciences of the United States of America 104, 1027-1032.

Pfaffl, M. W. (2001). A new mathematical model for relative quantification in real-time RT-PCR. Nucleic acids research 29, e45.

Wang, X., Wang, Y., Wu, X., Wang, J., Wang, Y., Qiu, Z., Chang, T., Huang, H., Lin, R. J., and Yee, J. K. (2015). Unbiased detection of off-target cleavage by CRISP R-Cas9 and TALENs using integrase-defective lentiviral vectors. Nature biotechnology.

Lin, Y., Cradick, T. J., Brown, M. T., Deshmukh, H., Ranjan, P., Sarode, N., Wile, B. M., Vertino, P. M., Stewart, F. J., and Bao, G. (2014). CRISPR/Cas9 systems have off-target activity with insertions or deletions between target DNA and guide RNA sequences. Nucleic acids research 42, 7473-7485.

SEQUENCE LISTING

| SEQ | Name | Sequence 5'-3' |
|---|---|---|
| | | sgRNA target |
| 1 | sgAPC(A) | AGGGCTATCTGGAAGATCAC |
| 2 | sgAPC(B) | CCATGCAGTGGAATGGTAAG |
| 3 | sgTP53(A) | GGGCAGCTACGGTTTCCGTC |
| 4 | sgTP53(B) | CAGAATGCAAGAAGCCCAGA |
| 5 | sgALK(A) | TGCAGCGAACAATGTTCTGG |
| 6 | sgALK(B) | AGAACATTGTTCGCTGCATT |
| 7 | sgEGFR(A) | CTGCGTGATGAGCTGCACGG |
| 8 | sgEGFR(B) | GAGCTGCGTGATGAGCTGCA |
| 9 | sgKRAS(A) | GAATATAAACTTGTGGTAGT |
| 10 | sgKRAS(B) | CTTGTGGTAGTTGGAGCTGG |
| 11 | sgEML4(a) | GACCTGAACAGCAAGTTTGT |
| 12 | sgALK(a) | GGCCTTGCTGAAACTTCCTT |
| 13 | sgAAVS1(A) | GTCCCCTCCACCCCACAGTG |
| 14 | sgAAVS1(B) | GTCACCAATCCTGTCCCTAG |
| | | Sequence 5'-3' (b) |
| | | ssODNA |
| 15 | APC-WT | CACTTGATAGTTTTGAGAGTCGTTCGATTGCCAGCTCCGTTCAGAGTGAACCATGCAGTGGAATGGTAAGTGcgATcATtAGtCCgAGcGAcCTTCCAGATAGCCCTGGACAAACCATGCCACCAAGCAGAAGTAAAACACCTCCACCACCTCCTCAAACAG |
| 16 | APC-MUT | CACTTGATAGTTTTGAGAGTCGTTCGATTGCCAGCTCCGTTCAGAGTGAACCATGCAGTGGAATGGTAAGTtGacTcgagAattcAGTGATCTTCCAGATAGCCCTGGACAAACCATGCCACCAAGCAGAAGTAAAACACCTCCACCACCTCCTCAAACAG |
| 17 | TP53-WT | CTCCTACACCGGCGGCCCCTGCACCAGCCCCCTCCTGGCCCCTGTCATCTTCTGTCCCTTCCCAGAAAACCTACCAGGGCAGCTAtGGaTtCGcCTcGGaTTCTTGCATTCTGGGACAGCCAAGTCTGTGACTTGCACGGTCAGTTGCCCTGAGGGGCTGGCTTCCATGAGACTTCAATGCCTGG |
| 18 | TP53-STOP | CTCCTACACCGGCGGCCCCTGCACCAGCCCCCTCCTGGCCCCTGTCATCTTCTGTCCCTTCCCAGAAAACCTACCAGGGCAGCTACGGTTgagaattcTCTTCTTGCATTCTGGGACAGCCAAGTCTGTGACTTGCACGGTCAGTTGCCCTGAGGGGCTGGCTTCCATGAGACTTCAATGCCTGG |

SEQUENCE LISTING

| SEQ | Name | |
|---|---|---|
| 19 | ALK-F1174F | GTAACTTTGTATCCTGTTCCTCCCAGTTTAAGATTT<br>GCCCAGACTCAGCTCAGTTAATTTTGGTTACATCCC<br>TCTCTGCTCTGCAGCAAgTTtAAtCAtCAaAACATa<br>GTTCGCTGCATTGGaGTGAGCCTGCAATCCCTGCCC<br>CGGTTCATCCTGCTGGAGCTCATGGCGGG |
| 20 | ALK-F1174L | GTAACTTTGTATCCTGTTCCTCCCAGTTTAAGATTT<br>GCCCAGACTCAGCTCAGTTAATTTTGGTTACATCCC<br>TCTCTGCTCTGCAGCAAATTaAAtCAtCAGAAtATc<br>GTcCGcTGCATTGGaGTGAGCCTGCAATCCCTGCCC<br>CGGTTCATCCTGCTGGAGCTCATGGCGGG |
| 21 | ALK-STOP | GTAACTTTGTATCCTGTTCCTCCCAGTTTAAGATTT<br>GCCCAGACTCAGCTCAGTTAATTTTGGTTACATCCC<br>TCTCTGCTCTGCAGCAAATagtgaattatcGAACAT<br>TGTTCGCTGCATTGaGGTGAGCCTGCAATCCCTGCC<br>CCGGTTCATCCTGCTGGAGCTCATGGCGGG |
| 22 | ALK-F1174L-<br>SWP | GTAACTTTGTATCCTGTTCCTCCCAGTTTAAGATTT<br>GCCCAGACTCAGCTCAGTTAATTTTGGTTACATCCC<br>TCTCTGCTCTGCAGCAAgTTaAAtCAtCAaAACATa<br>GTTCGCTGCATTGGaGTGAGCCTGCAATCCCTGCCC<br>CGGTTCATCCTGCTGGAGCTCATGGCGGG |
| 23 | ALK-F1174F-<br>SWP | GTAACTTTGTATCCTGTTCCTCCCAGTTTAAGATTT<br>GCCCAGACTCAGCTCAGTTAATTTTGGTTACATCcC<br>TCTCTGCTCTGCAGCAAATTtAAtCAtCAGAAtATc<br>GTcCGtTGCATTGGaGTGAGCCTGCAATCCCTGCCC<br>CGGTTCATCCTGCTGGAGCTCATGGCGGG |
| 24 | EGFR-T790T | CTCCCTCCCTCCAGGAAGCCTACGTGATGGCCAGCG<br>TGGACAACCCCCACGTGTGCCGCCTGCTGGGCATCT<br>GCCTCACCTCtACaGTcCAaCTgATtACcCAGCTCA<br>TGCCCTTCGGCTGCCTCCTGGACTATGTCCGGGAAC<br>ACAAAGACAATATTGGCTCCCAGTACCTGCTCAACT<br>GGTGTGTG |
| 25 | EGFR-T790M | CTCCCTCCCTCCAGGAAGCCTACGTGATGGCCAGCG<br>TGGACAACCCCCACGTGTGCCGCCTGCTGGGCATCT<br>GCCTCACCTCtACtGTaCAGCTtATaAtGCAaCTgA<br>TGCCCTTCGGCTGCCTCCTGGACTATGTCCGGGAAC<br>ACAAAGACAATATTGGCTCCCAGTACCTGCTCAACT<br>GGTGTGTG |
| 26 | KRAS-G12G | TAACCTTATGTGTGACATGTTCTAATATAGTCACAT<br>TTTCATTATTTTTATTATAAGGCCTGCTGAAAATGA<br>CTGAATATAAgtTgGTaGTgGTTGGcGCaGGaGGCG<br>TAGGCAAGAGTGCCTTGACGATACAGCTAATTCAGA<br>ATCATTTTGTGGACGAATATGATCCAACAATAGAGG<br>TAAA |
| 27 | KRAS-G12D | TAACCTTATGTGTGACATGTTCTAATATAGTCACAT<br>TTTCATTATTTTTATTATAAGGCCTGCTGAAAATGA<br>CTGAATATAAgtTaGtTgTGTcGTTGGtGCcGacGGCG<br>TAGGCAAGAGTGCCTTGACGATACAGCTAATTCAGA<br>ATCATTTTGTGGACGAATATGATCCAACAATAGAGG<br>TAAA |
| 28 | EML4-ALK | AGTGAACACAGTTGTGTTGTTCAATTTTTAAGGTAT<br>TTTTAGATGATAAATATTGATGTAAGTGGAGACAGT<br>TGACCTGAACAGCAAGTTCTTAGGCTCCATGGCACC<br>CAGGGTGCTTCCACCCAACCTTCCCTCCCTCCCTCG<br>TTCACGTGGGGTTATACTTGCAACACAGTCTGCTGG |
| 29 | AAVS1-deg (c) | GTGTCCCCGAGCTGGGACCACCTTATATTCCCAGGG<br>CCGGTTAATGTGGCTCTGGTTCTGGGTACTTTTATC<br>TGTCCCCTCCACCCCACANNNNatNNNNgtcGACAG<br>GATTGGTGACAGAAAAGCCCCATCCTTAGGCCTCCT<br>CCTTCCTAGTCTCCTGATATTGGGTCTAACCCCCAC<br>CTCCTGTTAGGCA |

-continued

| SEQUENCE LISTING | | |
|---|---|---|
| SEQ | Name | |
| qPCR primers | | |
| 30 | APC_Ctrl_FW | GCTGAAGATCCTGTGAGCGA |
| 31 | APC_Ctrl_RV | TTGTGCCTGGCTGATTCTGA |
| 32 | APC_cbc_FW | AGACCCCACTCATGTTTAGCAG |
| 33 | APC_cbc_WT_RV | GGTCGCTCGGACTAATGATCG |
| 34 | APC_cbc_STOP_RV | GGAAGATCACTGAATTCTCGAGTCA |
| 35 | TP53_Ctrl_FW | GACCCAGGGTTGGAAGTGTC |
| 36 | TP53_Ctrl_RV | CTAGGATCTGACTGCGGCTC |
| 37 | TP53_cbc_FW | CAGGTCCAGATGAAGCTCCCA |
| 38 | TP53_cbc_WT_RV | GAATCCGAGGCGAAAGCCA |
| 39 | TP53_cbc_STOP_RV | TCCCAGAATGCAAGAAGAGAATTCTC |
| 40 | ALK_Ctrl_FW/ ALK_cbc_FW | GCCCATGTTTACAGAATGCCTTT |
| 41 | ALK_Ctrl_RV | CCCCAATGCAGCGAACAATG |
| 42 | ALK_cbc_WT_RV | GCAGCGAACTATGTTTTGATGATTAAAC |
| 43 | ALK_cbc_MUT_RV/ ALK_cbc_WT_SWP_RV | CAATGCAACGGACGATATTCTGA |
| 44 | ALK_cbc_STOP_RV | CAGCGAACAATGTTCGATAATTCACT |
| 45 | ALK_cbc_MUT_SWP_RV | GCAGCGAACTATGTTTTGATGATTtAAC |
| 46 | EGFR_Ctrl_FW | TGCTTCCCCCATTCAGGACT |
| 47 | EGFR_Ctrl_RV | CTCCTTGCACCTCCTCACTG |
| 48 | EGFR_cbc_RV | CCTTCCCTGATTACCTTTGCGA |
| 49 | EGFR_cbc_T790T_FW | CACCTCTACAGTCCAACTGATTACC |
| 50 | EGFR_cbc_T790M_FW | CTCTACTGTACAGCTTATAATGCAACTG |
| 51 | KRAS_Ctrl_FW | ATCCTTTGAGAGCCTTTAGCCG |
| 52 | KRAS_Ctrl_RV | CCAGTTGACTGCAGACGTGTA |
| 53 | KRAS_cbc_G12G_RV | CTGCGCCAACCACTACCAAC |
| 54 | KRAS_cbc_G12D_RV | GTCGGCACCAACGACAACT |
| 55 | KRAS_cbc_FW | TATTAAAAGGTACTGGTGGAGTATTTGAT |
| 56 | EML4_ALK_FW | CTCGTGGTAACATCAGAACAGAGA |
| 57 | EML4_ALK_RV | TGCCATGGAGCCTAAGAACTTG |
| PCR primers for surveyor assay and RFLP | | |
| 58 | APC fw | AGCTGAAGATCCTGTGAGCG |
| 59 | APC rv | AATGGCTCATCGAGGCTCAG |
| 60 | AAVS1 fw | CATCTTCCAGGGGTCCGAGA |
| 61 | AAVS1 rv | TCAGTGAAACGCACCAGACG |

-continued

SEQUENCE LISTING

| SEQ | Name | |
|---|---|---|
| | PCR primers for APC deep sequencing | |
| 62 | APC 1_FW | GATTGCCAGCTCCGTTCAG |
| 63 | APC 1_RV | ATTTACTGCAGCTTGCTTAGGT |
| 64 | APC 2_FW | TGCTCAGACACCCAAAAGT |
| 65 | APC 2_RV | GTTTTACTTCTGCTTGGTGGC |
| | PCR primers for AASV1 deep sequencing | |
| 66 | AAVS1ds_FW (a) | *AATGATACGGCGACCACCGAGATCT*ACACTCTTTCCCTACACGACGCTCTTCCGATCTGTTAATGTGGCTCTGGTTCTGG |
| 67 | AAVS1ds_RV (a) | *CAAGCAGAAGACGGCATACGAGAT*CGTGATGTGACTGGAGTTCAGACGTGTGCTCTTCCGATCTGGTGGGGGTTAGACCCAATATC |
| | Primers, probes and blocking oligonucleotide for TaqMan PCR | |
| 68 | taqEGFRfw | TCCCTCCAGGAAGCCTACG |
| 69 | taqEGFRfw | CCTTCCCTGATTACCTTTGCGA |
| 70 | T790T-probe-FAM | CCAACTGATTACCCAGCTCATGCCC |
| 71 | T790M-probe-ABY | GCTTATAATGCAACTGATGCCCTTCGG |
| 72 | EGFR-T790-blocking (b) | TCCACCGTGCAGCTCATCACGCAG |

(a) Sequence from Choi and Meyerson (2014), Nat Commun 5, 3728
(b) Mutations compared to the endogenous sequence are indicated in lowercase letters
(c) The "N" nucleotides refer to degenerate nucleotides selected from A, C, G and T
All the sequences from the sequence listing are reported as 5'-3'.

The invention claimed is:

1. A method for labeling CRISPR Type II-Cas endonuclease-treated eukaryotic cells, comprising the steps of:
   a) providing eukaryotic cells or a composition comprising eukaryotic cells;
   b) bringing into contact said cells or said composition with:—
      (i) at least one Clustered Regularly Interspaced Short Palindromic Repeats (CRISPR)-CRISPR associated (Cas)(CRISPR-Cas) Type II-Cas endonuclease capable of targeting a genomic region of interest in said cells, or a vector capable of expressing said endonuclease in said cells;
      (ii) at least one first donor nucleic acid with homology regions in said genomic region of interest for homology-directed repair (HDR) and comprising, one or more silent mutation(s), and optionally one or more non-silent mutation(s); and
      (iii) at least one second donor nucleic acid with homology regions in said genomic region of interest for homology-directed repair (HDR) and comprising one or more silent mutation(s), but distinct from the silent mutations introduced by the first donor nucleic acid, said silent mutation(s) introduced by the second donor nucleic acid being at the same position(s) within the genomic region of interest or at different position(s) from the silent mutation(s) introduced by the first donor nucleic acid;
   thereby labeling the endonuclease-treated cells.

2. The method according to claim 1, wherein the first and/or second nucleic acid is/are single-stranded oligodeoxyribonucleotide(s) (ssODNA).

3. The method according to claim 1, wherein the silent mutation(s) are within an open reading frame (ORF) or exon of a gene coding for a protein of interest.

4. The method according to claim 1, wherein said cell(s) is/are mammalian cell(s).

5. A method for detecting a population of CRISPR Type II-Cas endonuclease-treated eukaryotic cells, comprising the steps of:

a) providing at least:
- a first population of Clustered Regularly Interspaced Short Palindromic Repeats (CRISPR)-CRISPR associated (Cas)(CRISPR-Cas) Type II-Cas endonuclease-treated eukaryotic cells comprising one or more silent mutation(s) introduced in a genomic region of interest by homology-directed repair (HDR), thereby providing a first signature; and
- a second population of Clustered Regularly Interspaced Short Palindromic Repeats (CRISPR)-CRISPR associated (Cas)(CRISPR-Cas) Type II-Cas endonuclease-treated eukaryotic cells, comprising one or more silent mutation(s) introduced in the same genomic region of interest by HDR, wherein said silent mutation(s) in the second population of Clustered Regularly Interspaced Short Palindromic Repeats (CRISPR)-CRISPR associated (Cas) (CRISPR-Cas) Type II-Cas endonuclease-treated eukaryotic cells are distinct from the silent mutation(s) of the first population, said silent mutation(s) of the second population being at the same position(s) within the genomic region of interest or at different position(s), thereby providing a second signature;

b) determining said first and second signature; and c) comparing said first and second signature, thereby detecting said first population of endonuclease-treated cells.

6. The method according to claim 5, wherein step b) is achieved by amplifying said genomic region of interest.

7. The method according to claim 5, wherein said cell(s) is/are mammalian cell(s).

* * * * *